(12) United States Patent
Coquet

(10) Patent No.: US 11,478,418 B2
(45) Date of Patent: Oct. 25, 2022

(54) **FAT AND/OR WAX ACTIVATED BY MEANS OF THE WATER-INSOLUBLE FRACTION OF *CARICA PAPAYA* SAP**

(71) Applicant: ISP INVESTMENTS LLC, Wilmington, DE (US)

(72) Inventor: Corinne Coquet, Cipieres (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 984 days.

(21) Appl. No.: 16/082,670

(22) PCT Filed: Mar. 7, 2017

(86) PCT No.: PCT/EP2017/055350
§ 371 (c)(1),
(2) Date: Sep. 6, 2018

(87) PCT Pub. No.: WO2017/153422
PCT Pub. Date: Sep. 14, 2017

(65) Prior Publication Data
US 2019/0307670 A1    Oct. 10, 2019

(30) Foreign Application Priority Data

Mar. 8, 2016  (FR) .................................. 1600394

(51) Int. Cl.
*A61K 8/92* (2006.01)
*A61K 8/9789* (2017.01)
*A61K 8/37* (2006.01)
*A61K 8/66* (2006.01)
*A61Q 19/08* (2006.01)
*C11B 15/00* (2006.01)
*A61K 8/97* (2017.01)

(52) U.S. Cl.
CPC ................ *A61K 8/922* (2013.01); *A61K 8/37* (2013.01); *A61K 8/66* (2013.01); *A61K 8/97* (2013.01); *A61K 8/9789* (2017.08); *A61Q 19/08* (2013.01); *C11B 15/00* (2013.01); *A61K 2800/805* (2013.01)

(58) Field of Classification Search
None
See application file for complete search history.

(56) References Cited

U.S. PATENT DOCUMENTS

| 7,211,269 B2 | 5/2007 | Dal Farra et al. |
| 7,396,815 B2 | 7/2008 | Dal Farra et al. |
| 8,674,072 B2 | 3/2014 | Dal Farra et al. |
| 2012/0220541 A1 | 8/2012 | Dal Farra et al. |

FOREIGN PATENT DOCUMENTS

| FR | 2817748 A1 | 6/2002 |
| FR | 2827170 A1 | 1/2003 |
| FR | 2837098 A1 | 9/2003 |
| FR | 2841781 A1 | 1/2004 |
| FR | 2846883 A1 | 5/2004 |
| FR | 2853834 A1 | 10/2004 |
| FR | 2944526 A1 | 10/2010 |
| FR | 2951946 A1 | 5/2011 |
| FR | 2956818 A1 | 9/2011 |

OTHER PUBLICATIONS

Dominguez de Maria, et al., Biotechnology Advances, 24:493. (Year: 2006).*
PCT, European Patent Office, International Search Report (English Translation), International Application No. PCT/EP2017/055350, 4 pages, dated May 15, 2017.
PCT, European Patent Office, Written Opinion of the International Searching Authority (English Translation), International Application No. PCT/EP2017/055350, 7 pages, dated May 15, 2017.
Abousalham, A. et al., "Zymogram of Pancreatic Lipases," Analytical Biochemistry, 218, pp. 234-236, 2000.
Azarkan, M. et al., "Fractionation and purification of the enzymes stored in the latex of *Carica papaya*," Journal of Chromatography B, 740, pp. 229-238, 2003.
Dominguez de Maria, P. et al., "*Carica papaya* lipase (CPL): An emerging and versatile biocatalyst," Biotechnology Advances 24, pp. 493-499, 2006.
Fuertes, L. et al., "Immunohistochemistry in Dermatopathology: A Review of the Most Common Used Antibodies (Part I)," ACTAS Dermo-Sifiliográficas, 104 (2), pp. 99-127, 2013.
Gilbert, E.J. et al., "Purification and properties of extracellular lipase from *Pseudomonas aeruginosa* EF2," Journal of General Microbiology, 137, pp. 2223-2229, 1991.
Giordani, R. et al., "Tributyroylglycerol Hydrolase Activity In *Carica papaya* And Other Latices," Phytochemistry, vol. 30, No. 4, pp. 1069-1072, 1991.
Mukherjee, K.D., "Lipase-catalyzed synthesis of designer lipids with improved nutritional properties," Food, Nutrision and Well Being, pp. 167-169, 1998.
Paladini, R.D. et al., "The Functional Diversity of Epidermal Keratins Revealed by the Partial Rescue of the Keratin 14 Null Phenotype by Keratin 16," The Journal of Cell Biology, vol. 146, No. 5, pp. 1185-1201, 1999.
Paques, F.W. et al., Characterization of the lipase from *Carica papaya* residues, Brazilian Journal of Food Technology, vol. 11, No. 1, pp. 20-27, 2008.

(Continued)

*Primary Examiner* — Michael Barker
(74) *Attorney, Agent, or Firm* — Thompson Hine LLP

(57) ABSTRACT

The invention relates to a method for obtaining the water-insoluble fraction of *Carica papaya* sap, enriched with *Carica papaya* lipase, the water-insoluble fraction obtainable by this method, a method for the preparation of an activated fat and/or an activated wax by means of said water-insoluble fraction of the *Carica papaya* sap, the activated fat and/or the activated wax capable of being obtained by this method, a composition combining said activated fat and/or said activated wax, as well as the cosmetic use of these products.

2 Claims, 5 Drawing Sheets

(56) References Cited

OTHER PUBLICATIONS

Rivera, I. et al., Plant Lipases: Partial Purification of *Carica papaya* Lipase, Methods in Molecular Biology, vol. 681, pp. 115-122, 2012.
Taylor, M.A.J. et al., "cDNA cloning and expression of *Carica papaya* prochymopapain isoforms in *Escherichia coli*," Plant Science, 145, pp. 41-47, 1999.
Villeneuve, P. et al., *Carica papaya* Latex Lipase: sn-3 Stereoselectivity or Short-Chain Selectivity? Model Chiral Triglycerides Are Removing The Ambiguity, Journal of the American Oil Chemists' Society (JAOCS), vol. 72, No. 6, pp. 753-755, 1995.
Yadav, R.P. et al., "Rapid Zymogram for Lipase," BioTechniques, 24, pp. 754-756, 1998.

\* cited by examiner

U.S. 11,478,418 B2

FAT AND/OR WAX ACTIVATED BY MEANS OF THE WATER-INSOLUBLE FRACTION OF *CARICA PAPAYA* SAP

TECHNICAL FIELD

This invention relates to the field of cosmetics. More particularly, the invention relates to activated fats and/or activated waxes administrable by dermal application/route, said activated fats and/or activated waxes being useful in cosmetics, in particular for delaying the appearance or limiting signs of skin aging, protecting the skin and/or superficial body surfaces against all types of external aggressions, and/or promoting cell differentiation at the cutaneous level, or strengthening the barrier function of the skin and/or superficial body surfaces.

BACKGROUND OF THE INVENTION

The skin is a vital organ providing multiple functions such as sensory and protective functions as well as immune, metabolic or thermoregulatory functions against multiple external aggressions (barrier function). These roles are made possible thanks to a structure in three distinct superimposed compartments: the epidermis, the dermis and the hypodermis. The epidermis is a surface epithelium that constitutes the outer structure of the skin and ensures its protective function. This function is ensured by the cohesion of the epithelial cells and by the production of a filamentous and resistant protein, keratin. The dermis is a connective tissue made up of a fundamental substance wherein fibroblasts, collagen fibers and elastin fibers, protein fibers synthesized by fibroblasts are bathed. The collagen fibers provide a large part of the strength of the dermis, they contribute to the elasticity and especially to the tone of the skin and/or mucous membranes. Below the dermis is a layer of adipose tissue: the hypodermis.

The skin, like all other organs, is subject to aging. The factors involved in the skin aging method are varied and numerous. The phenomenon of chronological aging of the skin is accompanied, inter alia, by a slowing down of cellular functions and the appearance of structural abnormalities in certain proteins of the extracellular matrix.

The skin becomes less supple, finer, often dry and it loses its elasticity, which is accompanied by wrinkles and fine lines.

In the epidermis, the slowing down of keratinocyte proliferation and differentiation with age is a factor that explains the thinning of the skin during aging. The epidermis atrophies, the skin loses its protective abilities. Dermal fibroblasts are also altered, and there is a decrease in the production of extracellular matrix proteins, such as collagen or elastin.

Chronic exposure to ultraviolet and other aggressive environmental factors accelerates and aggravates the aging phenomenon of the skin. We are speaking of photo-aging.

One of the mechanisms playing a major role in the aging method is the accumulation of oxidative damage in essential molecules such as in lipid membranes, proteins, DNA, and more particularly in mitochondrial DNA. Thus, one of the important consequences of the accumulation of these damages is a reduction in the ability of the cell to produce ATP.

For many years, health and cosmetic professionals have been looking for ways to fight or, at least, to reduce the phenomena of skin aging, as well as ways to increase the skin's resistance to external aggressions and to the stress which it suffers daily.

In cosmetics, oils are the basis of the concept of natural cosmetics. Vegetable oils obtained through a natural treatment without the addition of synthetic chemicals are traditionally used for their properties of hydration and protection.

Because of their specific composition, the oils most used in cosmetics are oils composed of long-chain polyunsaturated acids, in particular gamma-linolenic acid, which plays a specific role in the fluidity of membranes, the reduction of trans-epidermal water losses, and the prevention of skin aging. Indeed, some fatty acids are likely to improve or maintain the degree of hydration of the skin.

Oils are most often used as an excipient and not as an active ingredient. However, the Applicant has previously developed a composition, especially useful for cosmetic purposes, comprising, as active ingredient, in a physiologically acceptable medium, at least the combination of a specific diacylglycerol (abbreviated as "DAG") and a particular fatty alcohol. This composition is described and claimed in the patent application PCT/FR2004/000944, published under the reference WO 2004/093832 A2, in the name of the Applicant.

Diacylglycerols (DAG) are compounds specifically described in the Prior Art for their marker properties. They play a fundamental role, in particular through the action they exert on a protein kinase C, and thus have the function of cellular activator.

As disclosed in patent application WO 2004/093832, the reaction method to obtain DAGs may be a chemical reaction carried out in an acidic or alkaline medium such as, for example, the hydrolysis of triglyceride fats. This hydrolysis can also be carried out enzymatically, such as, for example, a biochemical reaction using a hydrolase such as a lipase. Preferably, the DAGs used in the compositions of WO 2004/093832 are obtained from fats (animal, vegetable or synthetic oils) comprising triglycerides having undergone enzymatic hydrolysis, specifically by lipases.

Lipases are enzymes that hydrolyze glycerol esters. Several types of lipase are determined according to their different reaction rate levels. These enzymes can also be classified into several groups, according to their different specificities: with respect to the substrate; position specificity or regioselective; specificity with respect to the nature of fatty acids or typo-selectivity; specificity with respect to a position or stereospecificity.

Some lipases have no specific specificity. Others are regioselective: thus, for example, pancreatic lipase and lipases of microbial origin, *Aspergillus, Rhysopus* or *Rhizomucor miehei* are 1,3-selective lipases. Regioselective lipases are of common industrial use both in the fat industry and in detergents. Other lipases are stereospecific, such as the *Candida* lipase, which has a stereospecificity of the sn2 type. The sn nomenclature determines the sn1, sn2 and sn3 positions of the triglyceride skeleton according to the asymmetrical carbon configuration presented in the Fisher projection.

In WO 2004/093832, a stereospecific lipase of the sn3 type (i.e., which allows the hydrolysis of triglycerides in position 3) is advantageously used. This lipase thus hydrolyzes the triglycerides at the 3-position, preferentially forming 1,2-DAG. The lipase used may be of plant origin (*Carica papaya*) or microbial (*Penicellium cyclopium*). According to a preferred embodiment, the hydrolysis of the triglycerides is carried out in WO 2004/093832 with a lipase of *Carica papaya* (Villeneuve et al., *JAOCS*, 72, 6:753.1995).

However, although the compositions obtained by implementing the teaching of patent application WO 2004/093832 have, in particular, satisfactory cosmetic properties at the cutaneous level, the Applicant has been endeavoring, for more than ten years, to improve the method for preparing these compositions, which method is exemplified in Example 1 of WO 2004/093832. More specifically, and as indicated in this Example 1, the enzymatic hydrolysis reaction to obtain 1,2-DAG is possible with raw *papaya* sap, however the use of a purified preparation of this sap after solubilization in an aqueous medium, and with polyol or lyophilized preservation. Indeed, the method of preparation that is the object of Example 1 of WO 2004/093832, if it works, there are a number of practical difficulties. Indeed, with regard to the use of a raw *papaya* sap, this is particularly disadvantageous in view of the fact that raw *papaya* sap contains not only the lipase of interest but also proteases (among which is papain, a protease cysteine) which are likely to degrade the lipase or, at the very least, negatively impact its enzymatic activity.

It is therefore logical that Example 1 of WO 2004/093832 favors the use of a purified preparation of this sap after solubilization in an aqueous medium, preserved in a polyol (for example in sorbitol) or freeze-dried. Regarding the latter possibility, it is known to the man skilled in the art that lyophilizates present a number of disadvantages, among which are their extreme sensitivity to atmospheric moisture and their complex (and therefore expensive) manufacturing method.

With regard to the technical solution of using a purified preparation of *papaya* sap after solubilization in an aqueous medium and preservation in a polyol (such as sorbitol), it turns out that this technique has the particular disadvantage of requiring a complex treatment subsequent to partial hydrolysis of triglycerides. In fact, in order to stop the partial hydrolysis reaction of the triglycerides, it is necessary to carry out several washing steps of the aqueous medium containing the *Carica papaya* lipase preserved in the polyol, especially using organic solvents.

Moreover, the Applicant has discovered that the *Carica papaya* lipase solubilized in an aqueous medium and preserved in a polyol had undergone freezing and, consequently, could barely—or even could not—be preserved in frozen form, whereas this is would be eminently desirable, with a view to ensuring good quality, convenient and inexpensive preservation of the *Carica papaya* lipase over time.

SUMMARY OF THE INVENTION

Through research, the Applicant has developed a real technological platform to overcome all or part of the aforementioned drawbacks. This technological platform is mainly based on obtaining and using the water-insoluble (not soluble in water) fraction of the *Carica papaya* sap. Consequently, the object of this invention is a method for obtaining the water-insoluble fraction of *Carica papaya* sap, enriched with *Carica papaya* lipase, said method comprising the following steps:

a) suspending dried raw *Carica papaya* sap in distilled water, advantageously in a weight ratio of dried raw *Carica papaya*/distilled water comprised of between about 0.01 and about 0.5 (preferably between 0.01 and 0.5), preferably between about 0.05 and about 0.25 (preferably between 0.05 and 0.25), preferably between about 0.08 and about 0.2 (preferably between 0.08 and 0.2), and particularly preferably about 0.1 (preferably 0.1), b) centrifuging the suspension obtained in step a) so as to obtain a pellet containing said water-insoluble fraction of the *Carica papaya* sap, advantageously for a time period comprised of between about 5 minutes and about 90 minutes (preferably between 5 minutes and 90 minutes), preferably between about 15 and about 60 minutes (preferably between 15 minutes and 60 minutes), preferably between about 20 and about 40 minutes (preferably between 20 and 40 minutes), and advantageously at a rotational speed comprised of between around 2000 and around 6000 rpm (preferably between 2000 and 6000 rpm), preferably between around 3000 and around 5000 rpm (preferably between 3000 and 5000 rpm), preferably around 4000 rpm (preferably 4000 rpm).

c) recovering the pellet containing said water-insoluble fraction of the *Carica papaya* sap, enriched with *Carica papaya* lipase.

In a particularly advantageous embodiment, said method comprises, after step a) and before step b), the following step:

a') agitating the suspension obtained in step a) during a time period comprised of between about 15 minutes and about 240 minutes (preferably between 15 minutes and 240 minutes), advantageously for a time period of between about 30 minutes and about 180 minutes (preferably between 30 minutes and 180 minutes), preferably between about 60 minutes and about 150 minutes (preferably between 60 minutes and 150 minutes), and particularly preferably about 120 minutes (preferably 120 minutes), and at a temperature comprised of between about 10° C. and about 30° C. (preferably between 10° C. and 30° C.), and at a temperature of between about 15° C. and about 25° C. (preferably between 15° C. and 25° C.), preferably at room temperature.

By room temperature a temperature comprised of between about 20° C. and about 25° C. is meant (preferably between 20° C. and 25° C.), advantageously a temperature of about 20° C. (preferably 20° C.)

Preferably, said method comprises, after step b) and before step c), the following step:

b') drying the wet pellet until a particulate powder is obtained;

the water-insoluble fraction of *Carica papaya* sap, enriched with *Carica papaya* lipase, being recovered in step c), in the form of particulate powder.

Another object of the invention relates to the water-insoluble fraction of *Carica papaya* sap enriched with *Carica papaya* lipase, obtainable by the aforementioned method.

The invention also relates to the water-insoluble fraction of *Carica papaya* sap enriched with *Carica papaya* lipase, obtained directly by the above method.

Particularly advantageously, the Applicant has discovered that this water-insoluble fraction of *Carica papaya* sap enriched with *Carica papaya* lipase, could be preserved simply by freezing. In addition, the method for obtaining this water-insoluble fraction of *Carica papaya* lipase-enriched *Carica papaya* sap, is extremely simple to implement and inexpensive.

The invention also relates to the use of the water-insoluble fraction of the *Carica papaya* sap according to this invention for enriching a fat with diacylglycerols (and thus obtaining an activated fat) and/or a wax with fatty alcohols (and thus obtaining an activated wax).

Another object of the invention relates to a method for preparing a diacylglycerol-enriched fat (activated fat), said method comprising the following steps:

i) mixing a fat with water or with a saline solution preferably containing a divalent ion, such as a calcium or magnesium ion, in a volume ratio of water or saline solution/fat comprised of between about 0.005 and about 0.5 (preferably between 0.005 and 0.5), preferably between about 0.01 and about 0.4 (preferably between 0.01 and 0.4), ii) maintaining this mixture under agitation (preferably with vigorous agitation, preferably at a speed of around 2000 to around 3000 rpm (preferably from 2000 to 3000 rpm); said vigorous agitation being advantageously obtained by means of an apparatus promoting emulsions) until an emulsion is obtained between the fat and water, at a temperature comprised of between about 30° C. and about 70° C. (preferably between 30° C. and 70° C.), advantageously about 50° C. (preferably 50° C.) preferably during a time period comprised of between about 1 and about 30 minutes (preferably between 1 and 30 minutes), preferably between about 5 and about 20 minutes (preferably between 5 and 20 minutes), and preferably about 10 minutes (preferably 10 minutes), iii) continue under agitation (preferably with moderate agitation, preferably at a speed of around 200 to around 300 rpm [preferably 200 to 300 rpm]) and at said temperature, bringing into contact the mixture obtained in the previous step with a given volume of the water-insoluble fraction of *Carica papaya* sap, enriched with *Carica papaya* lipase, obtained by implementing the method for obtaining the water-insoluble fraction of the above-mentioned *Carica papaya* sap, in a volume ratio of the water-insoluble fraction of *Carica papaya* sap/fat used comprised of between about 0.01 and about 0.2 (preferably between 0.01 and 0.2), advantageously between about 0.05 and 0.015 (preferably between 0.05 and 0.015), preferably about 0.1 (preferably 0.1), iv) maintaining said temperature and agitation for a time period of from about one hour to approximately six hours (preferably from one hour to six hours), advantageously from about two hours to about five hours (preferably from two hours to five hours), preferably for about four hours (preferably four hours), to obtain the diacylglycerol-enriched fat.

In a particularly preferred embodiment, this method for preparing a diacylglycerol-enriched fat (activated fat) comprises, after step iv), the following step:

v) filtering the mixture obtained in step iv), preferably using at least one gradient filter or at least one superposition of at least two filters of decreasing porosity, advantageously from around 500 µm to around 250 µm (preferably from 500 µm to 250 µm), so as to separate said water-insoluble fraction of *Carica papaya* sap, enriched in *Carica papaya* lipase, from the reaction medium containing the diacylglycerol-enriched fat.

Preferably, said method comprises, after step v), at least one of the following two steps, and advantageously both:

removal of the residual water present in the reaction medium containing the diacylglycerol-enriched fat by means of a drying agent such as anhydrous magnesium sulphate, and/or deodorizing and/or improving the shine of the diacylglycerol-enriched fat by means of an activated carbon.

This filtration step v) makes it possible to easily stop the partial hydrolysis reaction of the triglycerides contained in the fat without requiring a plurality of aqueous medium washing steps containing the lipase preserved in a polyol (as is the case with method of Example 1 of WO 2004/093832) and to avoid the use of organic solvents. Following this filtration step v), the water-insoluble fraction *Carica papaya* sap is also easily recovered and can be reused.

In general, the fact that is possible to use the water-insoluble fraction of the *Carica papaya* sap obtained by means of the aforementioned production method makes the post-partial hydrolysis handling of the fat relatively easy. In addition, the Applicant has discovered that the use of this water-insoluble fraction of the *Carica papaya* lipase-enriched *Carica papaya* sap, would preserve unsaturated fatty acids, which have advantageous cosmetic properties.

According to a particular embodiment, the water-insoluble fraction of the *Carica papaya* sap, enriched with *Carica papaya* lipase filtered in step v), is reused in step iii) of the method to prepare a diacylglycerol-enriched fat according to the invention.

Preferably, said fat is an animal, plant and/or marine origin oil, virgin or refined, advantageously virgin, said oil preferably being of plant and/or marine origin, preferably of plant origin.

It is particularly important to note that using the water-insoluble fraction of *Carica papaya* sap makes it possible for it to "work" with a virgin oil, namely to enrich (activate) a virgin oil with diacylglycerols, which is particularly desirable for reasons of safety and innocuousness (absence of organic solvents related to the refinement of oils etc.). In addition, the method for preparing a diacylglycerol-enriched fat according to the invention is particularly suitable for the enrichment of virgin oils, insofar as the unsaponifiable fraction of the virgin oil is not deteriorated by said method, the enzymatic activity used being of the triacylglycerol esterase type. This makes it possible to preserve the biological activity of the virgin oils after the enrichment method with diacylglycerols; this biological activity being further improved by said method.

Preferably, said fat is an oil comprising triglycerides having:

aliphatic hydrocarbon chains of a fatty acid having a carbon number of between 12 and 26, advantageously between 16 and 20, and particularly preferably between 16 and 18; said aliphatic hydrocarbon chain being linear or branched, advantageously linear, saturated or unsaturated, advantageously unsaturated, preferably with a number of unsaturations of between 1 and 6, and preferably of between 1 and 3; or mono- or polyhydroxylated and/or mono- or polymethoxylated and/or mono- or polyoxidized and/or mono- or poly-epoxylated chains.

According to a particularly preferred embodiment of this invention, an oil, preferably virgin is used as fat, selected from *Calophyllum inophyllum* oil, raspberry oil, *Camellia* oil, evening primrose oil, Brazil nut oil, baobab oil and olive oil, or a mixture of at least two of these oils; said oil, preferably virgin, being advantageously selected from *Calophyllum inophyllum* oil, raspberry oil, *Camellia* oil, evening primrose oil, Brazil nut oil, and baobab oil or a mixture of at least two of these oils; said oil, preferably virgin, being preferably selected from *Calophyllum inophyllum* oil, raspberry oil, evening primrose oil and baobab oil or a mixture of at least two of these oils; particularly preferably said fat being *Calophyllum inophyllum* oil, preferably virgin *Calophyllum inophyllum* oil.

The above diacylglycerols consist of 1,2-diacylglycerols and 1,3-diacylglycerols respectively represented by the following formulas (I) and (II):

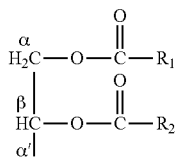

(I)

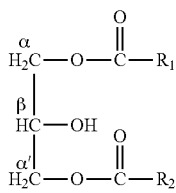

(II)

wherein R1 and R2 are:
aliphatic hydrocarbon chains of a fatty acid having a carbon number of between 12 and 26, advantageously between 16 and 20, and particularly preferably between 16 and 18 (in other words R1 and R2 represent aliphatic hydrocarbon chains whose carbon number is between 11 and 25, advantageously between 15 and 19, and particularly preferably between 15 and 17); said aliphatic hydrocarbon chain being linear or branched, advantageously linear, saturated or unsaturated, advantageously unsaturated, preferably with a number of unsaturations of between 1 and 6, and preferably of between 1 and 3; or mono- or polyhydroxylated, and/or mono- or polymethoxylated, and/or mono- or polyoxidized, and/or mono- or poly-epoxylated chains.

Preferably, said diacylglycerols comprise predominantly, and preferably consist essentially of, 1,2-diacylglycerols represented by the following formula (I):

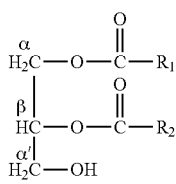

(I)

wherein R1 and R2 are:
aliphatic hydrocarbon chains of a fatty acid having a carbon number of between 12 and 26, advantageously between 16 and 20, and particularly preferably between 16 and 18 (in other words R1 and R2 represent aliphatic hydrocarbon chains whose carbon number is between 11 and 25, advantageously between 15 and 19, and particularly preferably between 15 and 17); said aliphatic hydrocarbon chain being linear or branched, advantageously linear, saturated or unsaturated, advantageously unsaturated, preferably with a number of unsaturations of between 1 and 6, and preferably of between 1 and 3; or mono- or polyhydroxylated, and/or mono- or polymethoxylated, and/or mono- or polyoxidized, and/or mono- or poly-epoxylated chains.

The invention also relates to a method for preparing a fatty alcohol-enriched wax (activated wax), implementing the method for preparing a diacylglycerol-enriched fat referred to above, by making the following adaptations:
a wax is used as a fat; and
in the place of a diacylglycerol-enriched fat, a fatty alcohol-enriched wax, advantageously fatty alcohols of formula (III), is obtained:

 (III)

wherein R" represents:
the aliphatic hydrocarbon chain of a fatty alcohol containing from 10 to 34 carbon atoms, preferably from 12 to 26 carbon atoms, and particularly preferably from 16 to 22 carbon atoms;
said aliphatic hydrocarbon chain being linear or branched, advantageously linear, saturated or unsaturated, preferably with a maximum of 6 unsaturations; or
a mono- or polyhydroxylated, and/or mono- or polymethoxylated, and/or mono- or polyoxidized, and/or mono- or poly-epoxylated chain.

In other words, the invention relates to a method for preparing a fatty alcohol-enriched wax (activated wax), said method comprising the following steps:

i') mixing a wax with water or with a saline solution preferably containing a divalent ion, such as a calcium or magnesium ion, in a volume ratio of water or saline solution/wax comprised of between about 0.005 and about 0.5 (preferably between 0.005 and 0.5), preferably between about 0.01 and about 0.4 (preferably between 0.01 and 0.4), ii') keeping this mixture under agitation until an emulsion is obtained between the wax and the water at a temperature comprised of between about 30° C. and about 70° C. (preferably between 30° C. and 70° C.) advantageously at about 50° C. (preferably at 50° C.), preferably during a time period comprised of between, advantageously about 1 to 30 minutes (preferably 1 to 30 minutes), preferably between about 5 to about 20 minutes (preferably between 5 and 20 minutes), and preferably about 10 minutes (preferably 10 minutes), iii') still under agitation and at said temperature, bringing into contact the mixture obtained in the preceding step with a given volume of the water-insoluble fraction of *Carica papaya* sap, enriched with *Carica papaya* lipase, obtained by implementing the method for obtaining the water-insoluble fraction of the aforesaid *Carica papaya* sap, in a volume ratio of the water-insoluble fraction of *Carica papaya* sap/wax used from about 0.01 to about 0.2 (preferably between 0.01 and 0.2), advantageously between about 0.05 and 0.015 (preferably between 0.05 and 0.015), preferably about 0.1 (preferably 0.1), iv') maintaining said temperature and agitation for a time period comprised of between about one hour and about six hours (preferably between one hour and six hours), advantageously between about two hours and about five hours (preferably between two hours and five hours), preferably for about four hours (preferably four hours), to obtain the wax enriched in fatty alcohols.

Preferably, this method comprises, after step iv'), the following step:

v') filtering the mixture obtained in step iv'), preferably using at least one gradient filter or at least one superposition of at least two filters of decreasing porosity, advantageously from around 500 μm to around 250 μm (preferably from 500 μm to 250 μm), so as to separate said water-insoluble fraction of *Carica* lipase-enriched

*Carica papaya* sap, from the reaction medium containing the fatty alcohol-enriched wax.

Preferably, said method comprises, after step v'), at least one of the following two steps, and advantageously both:
removal of the residual water present in the reaction medium containing the fatty alcohol-enriched wax by means of a drying agent such as anhydrous magnesium sulphate, and/or
deodorizing and/or improving the shine of the fatty alcohol-enriched wax by means of an activated carbon.

For the purposes of this invention, the wax is preferably selected from:
a wax of animal origin, such as, for example, beeswax,
a wax of mineral origin, or, preferably,
a wax of plant origin, such as jojoba wax, carnauba wax, candelilla wax, or a mixture(s) thereof;
said wax being advantageously jojoba wax.

In a particularly important embodiment, the invention also has for object a diacylglycerol-enriched fat, obtainable by the method for preparing a diacylglycerol-enriched fat according to the invention (see above). Of course, the invention also relates to a diacylglycerol-enriched fat directly obtained by the method for preparing a diacylglycerol-enriched fat according to the invention (see above).

According to a preferred embodiment, said fat has a diacylglycerol content comprised of between about 5% and about 30% (preferably between 5% and 30%), preferably between about 7% and about 18% (preferably between 7% and 30%), an acid index of from about 15 to about 50 mg/g (preferably from 15 to 50 mg/g) and a peroxide index from about 5 to 30 mg/g (preferably from 5 to 30 mg/g), preferably less than 20 mg/g.

This diacylglycerol-enriched fat is also called "activated fat".

As indicated above, this diacylglycerol-enriched fat (activated) is an oil of animal, plant and/or marine origin, virgin or refined, advantageously virgin, said oil being preferably of vegetable and/or marine origin, preferably of plant origin.

In a particularly preferred embodiment, this diacylglycerol-enriched fat (activated) is an oil, preferably virgin, selected from *Calophyllum inophyllum* oil, raspberry oil, *Camellia* oil, evening primrose oil, Brazil nut oil, baobab oil and olive oil, or a mixture of at least two of these oils; said oil, preferably virgin, being advantageously selected from *Calophyllum inophyllum* oil, raspberry oil, *Camellia* oil, evening primrose oil, Brazil nut oil and baobab oil or a mixture of at least two of these oils; particularly preferably said fat being *Calophyllum inophyllum* oil, preferably virgin *Calophyllum inophyllum* oil. Indeed, the Applicant has discovered that these (preferably virgin) diacylglycerol-enriched oils, and preferably 1,2 diacylglycerols, have particularly advantageous cosmetic properties when administered by cutaneous application. This is why the invention extends more broadly to a diacylglycerol-enriched oil (activated oil), advantageously 1,2 diacylglycerols, as defined above, independently from the method for enrichment with diacylglycerols used to produce the activated oil.

Another object of the invention relates to a fatty alcohol-enriched wax (activated wax), capable of being obtained by the method for preparing a fatty alcohol-enriched wax above. Naturally, the invention also relates to a fatty alcohol-enriched wax (activated wax), directly obtained by the method for preparing a fatty alcohol-enriched wax above.

The invention also has for object a cosmetic composition comprising, consisting essentially of or consisting of:
at least one diacylglycerol-enriched fat as mentioned above in an amount representing from $10^{-6}$% to 20% of the total weight of the composition, preferably in an amount representing from 10-4% to 10%, preferably in an amount representing from $10^{-3}$% to 2%, preferably from 0.01% to 5%, even more preferentially from 0.5 to 2.5% of the total weight of the final composition and
at least one physiologically acceptable excipient.

The invention also has for object a cosmetic composition comprising, consisting essentially of, or consisting of:
at least one fatty alcohol-enriched wax as mentioned above, in an amount representing from $10^{-6}$% to 10% of the total weight of the composition, preferably in an amount representing from 10-4% to 1%, preferably 0.01% % to 3%, even more preferably from 0.1 to 2.0% of the total weight of the final composition and
at least one physiologically acceptable excipient.

In a particularly significant embodiment, the invention also has for object a cosmetic composition comprising, consisting essentially of, or consisting of, a mixture of at least one diacylglycerol-enriched fat as mentioned above and at least one fatty alcohol-enriched wax as mentioned above, advantageously in a ratio by weight of fatty alcohol-enriched wax/diacylglycerol-enriched fat comprised of between 0.01 and 0.11, preferably between 0.02 and 0.08, and preferably about 0.03 (preferably 0.03).

The invention also has for object a cosmetic composition comprising, consisting essentially of, or consisting of:
a mixture of at least one diacylglycerol-enriched fat as mentioned above and at least one fatty alcohol-enriched wax as mentioned above, advantageously in a weight ratio of fatty alcohol-enriched wax/diacylglycerol-enriched fat comprised of between 0.01 and 0.11, preferably between 0.02 and 0.08, and preferably about 0.03 (preferably 0.03), and
at least one physiologically acceptable excipient.

The invention also has for object a cosmetic composition comprising, consisting essentially of, or consisting of:
a mixture of at least one diacylglycerol-enriched fat as mentioned above and at least one fatty alcohol-enriched wax as mentioned above, in an amount representing from $10^{-6}$% to 20% of the total weight of the composition preferably in an amount representing from 10-4% to 10%, preferably from 0.01% to 5%, even more preferentially from 0.5 to 2.5% of the total weight of the final composition and
at least one physiologically acceptable excipient.

The composition according to the invention may be applied by any appropriate route, in particular oral, or externally topical, and the formulation of the compositions will be adapted by the man skilled in the art.

Preferably, the compositions according to the invention are in a form suitable for topical application. These compositions must therefore contain a physiologically acceptable medium, that is to say, compatible with the skin and its appendages, without risk of discomfort during their application and covering all suitable cosmetic forms.

By topical application, it is meant to the application or spreading of the composition according to the invention on the surface of the skin or mucosa.

In the context of the invention, a physiologically acceptable excipient designates a vehicle suitable for contact with the outer layers of the skin or its appendages, that is to say which does not exhibit toxicity and does not cause irritation, undue allergic response or intolerance reaction. A physiologically acceptable excipient may comprise one or more compounds.

As a physiologically acceptable excipient commonly used in the intended field of application, mention may be made, for example, of adjuvants necessary for the formulation, such as solvents, thickeners, diluents, antioxidants, dyes, sunscreens, self-tanning agents, pigments, fillers, preservatives, perfumes, odor absorbers, essential oils, vitamins, essential fatty acids, surfactants, film-forming polymers, etc.

In all cases, the man skilled in the art will ensure that these adjuvants and their proportions are chosen in such a way as not to harm the desirable advantageous properties of the composition according to the invention.

A physiologically acceptable excipient may comprise one or more compounds.

The compositions for the implementation of the invention may be notably in the form of an aqueous, aqueous-alcoholic or oily solution, of an oil-in-water emulsion, water-in-oil or multiple emulsions; they may also be in the form of suspensions or even powders, suitable for application to the skin, mucous membranes, lips and/or hair.

These compositions may be more or less fluid and may also have the appearance of a cream, a lotion, a milk, a serum, an ointment, a gel, a paste or a foam. They can also be in solid form, as a stick or may be applied to the skin in the form of an aerosol.

As a physiologically acceptable excipient commonly used in the intended field of application, mention may be made, for example, of adjuvants necessary for the formulation, such as solvents, thickeners, diluents, antioxidants, dyes, sunscreens, self-tanning agents, pigments, fillers, preservatives, perfumes, odor absorbers, essential oils, vitamins, essential fatty acids, surfactants, film-forming polymers, etc.

In all cases, the man skilled in the art will ensure that these adjuvants and their proportions are chosen in such a way as not to harm the desirable advantageous properties of the composition according to the invention. These adjuvants may, for example, correspond to 0.01 to 20% of the total weight of the composition. When the composition according to the invention is an emulsion, the fatty phase can represent from 5 to 80% by weight and preferably from 5 to 50% by weight relative to the total weight of the composition. The emulsifiers and co-emulsifiers used in the composition are chosen from those conventionally used in the field under consideration. For example, they can be used in a proportion ranging from 0.3 to 30% by weight, relative to the total weight of the composition.

According to another advantageous embodiment of the invention, the active ingredient according to the invention can be encapsulated or included in a cosmetic vector such as liposomes or any other nanocapsule or microcapsule used in the field of cosmetics or adsorbed on powdered organic polymers, mineral supports like talcs and bentonites.

Advantageously, the composition according to the invention may comprise, in addition to the active ingredient according to the invention, at least one other active ingredient having cosmetic effects similar and/or complementary to those of the invention. According to the invention, this active ingredient is defined as an "additional active ingredient".

For example, the additional active ingredient(s) may be chosen from: anti-aging, firming, lightening, moisturizing, draining, microcirculation promoting agents, pharmaceutical agents, exfoliants, desquamative agents, that stimulate the extracellular matrix, activating energy metabolism, antibacterial, antifungal, soothing, anti-free radicals, anti-UV, anti-acne, anti-inflammatory, anesthetic agents, that provide a feeling of warmth, and a feeling of freshness and slimming.

Such additional agents may be selected from the groups comprising:

vitamin A and in particular retinoic acid, retinol, retinol propionate, and retinol palmitate;
vitamin B3 and more particularly niacinamide, tocopherol nicotinate;
vitamin B5, vitamin B6, vitamin B12, panthenol;
vitamin C, in particular ascorbic acid, ascorbyl glucoside, ascorbyl tetrapalmitate, magnesium and sodium ascorbyl phosphate;
vitamins E, F, H, K, PP, coenzyme Q10;
metalloproteinase inhibitors, or an activator of TIMPs;
DHEA, its precursors and derivatives;
amino acids such as arginine, ornithine, hydroxyproline, hydroxyproline dipalmitate, palmitoylglycine, hydroxylysine, methionine and its derivatives, N-acyl amino acid compounds;
natural or synthetic peptides, including di-, tri-, tetra-, penta- and hexapeptides and their lipophilic derivatives, isomers and complexed with other species such as a metal ion (e.g., copper, zinc, manganese, magnesium, and others). By way of examples, mention may be made of the peptides commercially known under the name MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or the synthetic peptide sequence Arg-Gly-Ser-NH2, marketed under the name ATPeptide™ by ASHLAND@;
*Artemia salina* extract, marketed under the name GP4G™ (FR2817748, ASHLAND®);
plant peptide extracts such as linseed extracts (Lipigenine™, patent FR2956818, ASHLAND®), soy bean, spelt, grapevine, rapeseed, flax, rice, maize, and pea extracts;
yeast extracts, for example Dynagen™ (patent FR2951946, ASHLAND®) or Actopontine™ (patent FR2944526, ASHLAND®);
dehydroacetic acid (DHA);
phystosterols of synthetic or natural origin;
salicylic acid and its derivatives, alpha- and beta-hydroxy acids, silanols;
amino sugars, glucosamine, D-glucosamine, N-acetyl glucosamine, N-acetyl-D-glucosamine, mannosamine, N-acetyl mannosamine, galactosamine, N-acetyl galactosamine;
polyphenol extracts, isoflavones, flavonoids, such as grape extracts, pine extracts, olive extracts;
lipids such as ceramides or phospholipids, oils of animal origin, such as squalene or squalane; vegetable oils, such as sweet almond, coconut, castor, jojoba, olive, rapeseed, peanut, sunflower, wheat germ, corn germ, soy bean, cotton, alfalfa, poppy, pumpkin, evening primrose, millet, barley, rye, safflower, passionflower, hazelnut, palm, apricot kernel, avocado, calendula; ethoxylated vegetable oils, and shea butter;
all UV screens and sunscreens;
cyclic AMP and its derivatives, activating agents of the adenylate cyclase enzyme and phosphodiesterase enzyme inhibiting agents, *Centella asiatica* extract, asiaticoside and asiatic acid, methyl xanthines, theine, caffeine and its derivatives, theophylline, theobromine, forskolin, esculin and esculoside, ACE inhibitors, Val-Trp peptide, neuropeptide Y inhibitors, enkephalin, extract of *Gingko biloba, Dioscorea* extract, rutin, yerba mate extract, guarana extract, oligosaccharides, polysaccharides, carnitine, ivy extract, fucus extract, extract hydrolyzed *Prunella vulgaris*, hydrolysed extract of *Celosia cristata, Anogeissus leiocarpus* extract, *Manihot utilisissima* leaf extract, palmitoylcarnitine, carnosine, taurine, elderberry extract, seaweed extract such as *Palmaria palmata* extract.

The object of the invention is also the cosmetic use of an effective amount of at least one diacylglycerol-enriched fat according to the invention, of at least one fatty alcohol-enriched wax according to the invention, or of a composition according to the invention, by cutaneous application, to:

delay the appearance or limit the signs of skin aging, and/or
protect the skin and/or its appendages against all types of external aggressions, and/or
promote epidermal differentiation, and/or
strengthen the barrier function of the skin and/or its appendages,
in a healthy human or animal individual (preferably mammalian), preferably human.

"Visible signs of skin aging" means any changes in the external appearance of the skin due to aging, such as, for example, fine lines and wrinkles, pigmentary defects such as age spots or lack of radiance, bags under the eyes, dark circles, withering, loss of elasticity, firmness and/or skin tone, but also any internal changes in the skin that do not systematically result in a change in external appearance such as for example, thinning of the skin, or any internal damage to the skin resulting from environmental stresses such as pollution and UV radiation.

The skin is an organ whose upper part, the stratum corneum and the hydrolipidic film that covers it, acts as a physical barrier protecting the external environment. This barrier role, more commonly known as "skin barrier function", is of major importance in tissue homeostasis. However, it is known that alterations in the barrier function result from external aggression by agents such as ultraviolet radiation (UVA and UVB), cold, drought, atmospheric pollution, certain chemical substances, etc. Alterations in the barrier function are also observed during aging of the skin and are due, among other things, to slowing down and to abnormal epidermal differentiation, which may lead to an increase in skin permeability.

The composition according to the invention makes it possible to fight against all these external aggressions, by favoring an optimal epidermal differentiation making it possible to maintain a functional histological structure and physiological permeability sufficient to maintain this essential barrier function represented by the skin.

The object of the invention is also a cosmetic treatment method for delaying the appearance or limiting the signs of skin aging and/or combating the cell aging phenomena at the cutaneous level and/or for protecting the skin and/or its appendages against all types of external aggressions and/or to promote cell differentiation at the cutaneous level and/or to reinforce the barrier function of the skin and/or its appendages, consisting of applying to at least part of the skin and/or its appendages an effective amount of the composition according to the invention, as defined above.

BRIEF DESCRIPTION OF THE FIGURES

For the sake of completeness, the experimental data obtained by the Applicant in order to characterize the water-insoluble fraction of *Carica papaya* sap are presented below, within the detailed description of the invention. This experimental data refer to FIGS. 1-4, which are briefly presented below.

DETAILED DESCRIPTION OF THE INVENTION

Definitions

Figure 1:
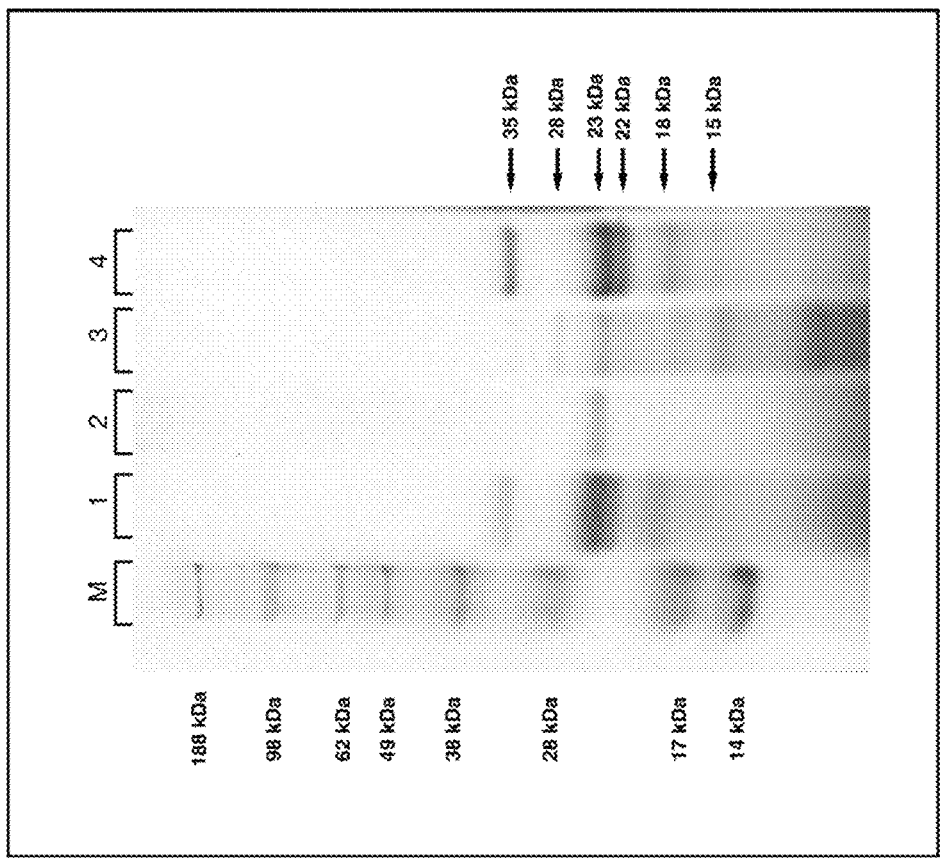
FIG. 1 is an electrophoretic profile of the proteins present in the *papaya* sap (1), in the water-insoluble fraction (also referred to as "non-water-soluble") of the *papaya* sap (2), in the soluble fraction in water (also referred to as "water-soluble") of *papaya* sap (3), commercial papain (Fluka) (4), and proteins of a molecular weight marker (Invitrogen) (M) on 12% polyacrylamide gel.

Fat. Within the meaning of this invention, a fat has the definition commonly accepted in the State of the Art, namely a substance composed of molecules having hydrophobic properties. Fats are mainly composed of triglycerides which are esters derived from a molecule of glycerol and three fatty acids. The other components form what is called the unsaponifiable fraction or the "unsaponifiable". The principal fats are:

oils which are in the liquid state at room temperature because they are mainly composed of unsaturated fatty acids which have low melting points;

fats that are pasty or solid at room temperature because they are mostly composed of saturated fatty acids that have higher melting points.

As indicated above, for the purposes of this invention, an oil of animal, vegetable and/or marine origin, virgin or refined, advantageously virgin, is used as a fat, said oil being preferably of plant and/or marine origin, preferably of plant origin.

Fats of marine origin. The marine fats may be of animal, plant, bacterial and/or may be algae (for example microalgae, as indicated below). By way of example, mention may be made of fish oils, such as shark liver oil and cod liver oil, and algae and microalgae oils such as haemotococcus pluvialis.

Oils of vegetable origin (or, more simply, "vegetable oils"). According to a particularly preferred embodiment of the invention vegetable oils are used, such as olive oil, rapeseed oil, soybean oil, corn oil, sweet almond oil, andiroba oil, Silversmiths Oil, babassu oil, laurel berry oil, borage oil, broccoli oil, buriti oil, *Calophyllum inophyllum* oil, *Camellia* oil, safflower oil, blackcurrant oil, hemp oil, coconut oil, cucumber seed oil, cranberry oil, raspberry pip oil, passion fruit oil kiwi seed oil, hazelnut oil, Brazil nut oil, shea olein oil, grape seed oil, apricot kernel oil, sesame oil, rice bran oil, nutmeg seed oil, tomato seed oil, baobab oil, evening primrose oil, *Camellia* oil, camelina oil, milk thistle oil, grape seed oil, carrot oil, St. John's wort oil, flaxseed oil, walnut oil, pomegranate seed oil, nigella seed oil, borage oil, squash seed oil, *Perilla* oil, green coffee bean oil, avocado oil, hibiscus oil, argan oil, safflower oil, rose hip oil, cloudberry oil, Chia (*Salvia hispanica*) oil. But also an oily macerate of flowers such as vanilla, St. John's wort, lily, carrot, *Bellis, Arnica*, aloe vera, calendula, prickly pear (non-exhaustive list). As indicated above, among these vegetable oils, those found during the implementation of the invention are preferred for their particularly interesting cosmetic properties, *Calophyllum inophyllum* oil (preferably virgin), raspberry oil (preferably virgin), *Camellia* oil (preferably virgin), evening primrose oil (preferably virgin), Brazil nut oil (preferably virgin), baobab oil (preferably virgin), and olive oil (preferably); with the stipulation that the first six are particularly preferred.

*Calophyllum inophyllum* Oil (*Calophyllum inophyllum* L.; Tamanu). *Calophyllum*, a tree dubbed Tamanu by the Tahitians and Fohara by the *malagasy*, produces a remarkable oil for its beneficial action on the skin. It is very aromatic, and this oil is traditionally used to treat many dermatological conditions (eczema, psoriasis, zoster . . . )

Numerous studies have shown that *Calophyllum* oil contains many active ingredients with disinfecting and protective properties, making this oil a valuable ally for skin problems.

The saponifiable fraction is composed of linoleic acid (30-35%), oleic acid (30-35%), palmitic acid (15-20%), stearic acid (15-20%).

The unsaponifiable fraction is composed of Inophyllin A: anti-bacterial, disinfectant action; Calaustraline and inophyllolide: powerful healing and skin repair; Polyphenols: antioxidants and healing action, they also have a very strong action on the venous circulation; vitamin E: natural antioxidant.

Baobab Oil (*Adansonia digitata*). Baobab oil is used in the Senegalese pharmacopoeia for its anti-allergic and anti-inflammatory properties. In cosmetics, this very emollient and soothing oil is particularly effective for dry, torn and chapped skin.

Renowned for healing and regeneration, it is recommended for the burn care. The saponifiable fraction is composed of linoleic acid (22-26%), oleic acid (30-40%), palmitic acid (20-25%), stearic acid (2-6%). The unsaponifiable fraction is composed of phytosterols (including beta-sitosterol) and vitamin E.

Brazil Nut Oil (*Bertholletia excelsa*). The Brazil nut or Amazon nut comes from a South American tree called: *Bertholletia excelsa*. A vegetable source of phospholipids, tocopherols and phytosterols, Brazil nut oil brings softness, comfort and elasticity to the skin while acting as a natural antioxidant.

The saponifiable fraction is composed of linoleic acid (40-45%), oleic acid (Omega-9) (30-35%), palmitic acid (10-15%), stearic acid (5-10%). The unsaponifiable fraction is composed of phytosterols (including beta-sitosterol): they maintain the structure and function of the cell membrane and reduce inflammation; Squalenes: the main components of the skin surface, they have emollient and antioxidant properties. Tocopherols: natural vitamin E, powerful antioxidants that prevent the rancidity of fatty acids and protect cells from free radical damage; Phospholipids: compounds similar to those that form cell membranes, emollient and protective properties; Selenium: trace element with antioxidant properties.

Evening Primrose Oil (*Oenothera biennis*). Evening primrose oil is very rich in linoleic acid and is one of the rare oils to contain gamma-linolenic acid. These essential fatty acids, reconstructors of cell membranes, have exceptional softening, revitalizing, restructuring and anti-wrinkle properties. Also rich in vitamin E, evening primrose oil protects the skin from premature aging.

The saponifiable fraction is composed of linoleic acid (70-75%), gamma-linolenic (5-10%) oleic acid (4-8%), palmitic acid (4-8%), stearic acid (1-4%).

The unsaponifiable fraction (1.5 to 2%) is composed of phytosterols: healing and restorative action, they also reduce inflammation; triterpenes: anti-radical action, they protect the tissues from degeneration; Sterols including vitamin E: natural antioxidants.

*Camellia* Oil (*Camellia sinensis* L.). *Camellia* oil, also called green tea oil is extracted from tea tree seeds. The vegetable oil of *Camellia* has nourishing, protective, softening and moisturizing properties for the skin.

The saponifiable fraction is composed of linoleic acid (5-10%), oleic acid (75-80%), palmitic acid (5-10%), stearic acid (1-5%).

The unsaponifiable fraction (1.5 to 2%) is composed of triterpenes; squalane; saponins as well as kaempferol and its glycosides: these are strongly anti-inflammatory compounds, such as quercetin. They help protect the body from damage caused by inflammatory conditions.

Raspberry Oil (*Rubus idaeus* L.). Raspberry oil has healing properties thanks to its exceptional content of essential fatty acids (Omega-3 and Omega-6), it is also used to relieve itching and eczema. Raspberry oil is also known to absorb some of the UVA and UVB rays, providing light protection to the sun. It is rich in antioxidants and carotenoids and is also an ideal oil for sun-care and after-sun repair.

The saponifiable fraction is composed of linoleic acid (50-55%) and alpha-linolenic acid (30-35%), oleic acid (Omega-9) (10-15%) palmitic acid (0-5%).

The unsaponifiable fraction is composed of vitamin E (about 5600 mg/kg): natural antioxidant; gallic acid: natural antioxidant; of carotenoids (beta-carotene, lutein, and cryptoxanthin): anti-radical action, they protect the tissues from degeneration.

Olive Oil (*Olea europaea* L.). The olive tree has been known for millennia for its exceptional longevity. It is also the first tree that is quoted in the history of the world.

Obtained by cold pressing of its pulp and not of its pits, olive oil is one of the oils richest in oleic acid. Nourishing, softening and emollient, we find olive oil in the composition of traditional Aleppo and Marseille soaps.

It is an excellent healing agent, it has a significant concentration of unsaponifiables (approximately 1 to 2%) that offer antioxidant, soothing and protective qualities against the harmful effects of weather and sun. Internally, olive oil has digestive and slightly laxative properties that make it recommended for digestive disorders and especially those of the stomach.

The saponifiable fraction is composed of linoleic acid (15-20%), oleic acid (55-60%), palmitic acid (15-20%), stearic acid (0-5%).

The unsaponifiable fraction is composed of phenolic compounds (hydroxytyrosol): majority antioxidants; phytosterols: healing and restorative action; squalenes: the main components of the skin surface, they have emollient and antioxidant properties, Vitamin E (alpha-tocopherol), Chlorophyll: natural antioxidants.

When the fat used for the purposes of this invention is an oil (preferred embodiment), this oil may be virgin or refined. According to a particularly preferred embodiment of the invention, at least one virgin oil is preferably used, and preferably a virgin vegetable oil. Indeed, the technological platform developed by the Applicant has the significant advantage of being able to obtain virgin oils, preferably virgin vegetable oils, enriched with diacylglycerols and/or fatty alcohols (cosmetic active ingredients) without the need to turn to refined oils.

Virgin vegetable oils. Vegetable oils called "virgin" are pure vegetable oils, extracted solely by mechanical methods from fruits, seeds, kernels, generally by first cold expression (at a maximum temperature of 60° C.) from a cultivated plant. These oils are characterized by their unsaponifiable and saponifiable fractions. The unsaponifiable fraction is the residual fraction which is insoluble in water but soluble in organic acids after saponification. The unsaponifiable fat content is generally in the range of 0.5 to 2%. It is a complex mixture comprising sterols, hydrocarbons (squalene, . . . ), triterpenes, fatty alcohols (waxes), liposoluble pigments, vitamins, etc.

The unsaponifiable fraction of vegetable oils finds applications in cosmetics for its biological properties. The saponifiable fraction of oils is characterized by fatty acids, glycerides and triglycerides. Fatty acids are of two types, saturated fatty acids, unsaturated fatty acids (monounsaturated/MUFA or polyunsaturated/PUFA). Using these virgin vegetable oils as fat is particularly preferred within the meaning of this invention.

Refined oils. Although, as indicated above, the use of a virgin oil, and preferably a virgin vegetable oil is preferred in the sense of this invention, the latter also works very well with refined oils. For an oil to be refined, it must undergo hot pressure. With pressing that takes place at a temperature of between 80° C. and 120° C. This produces a crude oil, which cannot be consumed as it is, it must undergo a long series of treatments in order to eliminate unwanted tastes and colors. The degumming step involves removing the substances that contribute to the instability and the production of foam and smoke during frying (free fatty acids, phospholipids), by stirring, with acidulated water, which will hydrolyze and thereby separate the substances. Then the taste is neutralized with a solution of soda. This is followed by bleaching at 90° C. with bleaching earth and filtering to rid the oil of its pigments. The method ends with deodorization using low-pressure water vapor to better preserve the qualities of the oil. In this way a clear, odorless refined oil with little flavor is obtained. These oils are only characterized by their saponifiable fraction, the unsaponifiable fraction being eliminated by the treatments.

The Applicant has discovered that the components of the unsaponifiable fraction, namely sterols, hydrocarbons (squalene, etc.), triterpenes, fatty alcohols (waxes), fat-soluble pigments, and vitamins (non-exhaustive list) make it possible to increase the biological (cosmetic) activity of the activated fats and compositions containing them according to this invention. This is one of the reasons why the use of a virgin oil (preferably a virgin vegetable oil), including this valuable unsaponifiable fraction, is particularly preferred with respect to this invention, the technological platform constituting this invention being quite suitable for the enrichment/activation of a virgin oil.

Activated Fat/Activated Oil. This invention aims in particular to obtain a diacylglycerol-enriched fat (preferably an oil), in particular 1,2-diacylglycerols; the diacylglycerols present in the fat/oil thus enriched acting as a cosmetic active ingredients, in the context of a cutaneous application. In other words, the diacylglycerol-enriched fats have a modified structure and increased biological (cosmetic) activity at the cutaneous level. This is why the fats/oils thus enriched are also called activated fats/activated oils.

Wax. A wax is an ester of ethylene glycol and two fatty acids or a monoester of fatty acid and of a long chain alcohol. The waxes may be of animal origin, such as beeswax, of plant origin, such as jojoba, carnauba, or candelilla wax, or of mineral origin.

The fatty alcohols are aliphatic alcohols with a long hydrocarbon chain having a single hydroxyl function in the terminal position. By fatty alcohol, the compounds of formula (III) is meant:

$$R''\text{—}OH \qquad (III)$$

wherein R" represents the aliphatic chain of a fatty alcohol. This fatty alcohol is constituted by a carbon chain comprising from 10 to 34 carbon atoms.

According to one particular embodiment of the invention, the fatty alcohols have a carbon chain whose carbon number is between 12 and 26. According to another preferred embodiment of the invention, the fatty alcohol has on its chain aliphatic between 16 and 22 carbon atoms.

Thus, these fatty alcohols will preferably be selected from the group consisting of saturated or unsaturated average size aliphatic chain fatty alcohols.

Furthermore, the aliphatic chain of fatty alcohols, that is to say the group R", may be a linear or branched carbon chain, and/or saturated or unsaturated, the number of unsaturation being between 1 and 6. The R" group may also be a mono- or polyhydroxylated and/or mono- or polymethoxylated and/or mono- or polyoxidized and/or mono- or polyepoxylated chain. It can thus be present in all the existing natural forms.

These fatty alcohols are found in large quantities in waxes. These waxes may be of animal origin, such as beeswax, or of plant origin, such as jojoba, carnauba, or candelilla wax, or of mineral origin.

Thus, for example, the controlled hydrolysis of jojoba oil wax (abbreviated as "jojoba wax", a wax that makes up more than 96% of jojoba oil) has the effect of releasing the main aliphatic fatty alcohols contained therein, which provides a mixture of fatty alcohols, of a saturated or unsaturated linear hydrocarbon chain.

In particular, the hydrolysis of the jojoba oil wax makes it possible to obtain a mixture of fatty alcohols of a high degree of purity having, in their aliphatic chain, between 16 and 22 carbon atoms.

Jojoba oil wax is the liquid wax contained in the Jojoba seed (*Simmondsia chinensis*), a bushy plant native to southern Arizona and California, as well as northwestern Mexico. Jojoba seeds have an oil yield of about 50% of their weight. Jojoba oil is a mixture of ceridic esters with chains of 36 to 46 carbon atoms. Each molecule consists of a fatty acid and a fatty alcohol linked by an ester bond. Jojoba oil is characterized by the presence of 10% oleic acid ($C_{18:1}$), 70% gadoleic acid ($C_{20:1}$), 15% erucic acid ($C_{22:1}$), 5% nervonic acid ($C_{24:1}$) and associated fatty alcohols, octacosenol ($C_{18:1}$), eicosenol ($C_{20:1}$), docosenol ($C_{22:1}$) and tetracosenol ($C_{24:1}$). Thus the controlled hydrolysis of jojoba wax has the effect of releasing the principal aliphatic fatty alcohols contained therein, which provides a mixture of saturated or unsaturated linear chain fatty alcohols.

Thus, for example, the controlled hydrolysis of jojoba wax (a wax that makes up more than 96% of jojoba oil) has the effect of releasing the principal aliphatic fatty alcohols and fatty acids contained therein, making it possible to obtain a wax enriched in saturated and unsaturated hydrocarbon-based fatty alcohols and fatty acids. In particular, hydrolysis of jojoba oil by this invention makes it possible to obtain a fatty alcohol-enriched wax and fatty acids having between 18 and 24 carbon atoms. This hydrolysis thus makes it possible to concentrate all the active ingredients that are capable of acting on the skin.

The mixture of fatty acids and fatty alcohols according to the invention will preferably be obtained from a hydrolysis of the waxes present in the jojoba oil (*Simmondsia chinensis*). This hydrolysis makes the release of the constituent fatty alcohols of this wax possible. This hydrolysis may be carried out enzymatically using a triacylglycerol hydrolase whose main activity is to hydrolyze the ester bond in order to release an alcohol and an acid. One of the particularly advantageous possibilities of this invention is to use the same lipase as that used for the hydrolysis of triacylglycerols.

Preferably according to the invention, the active ingredients constituting the association, i.e., the diacylglycerol-enriched oil and a wax enriched in fatty acids and fatty alcohols, will be of plant, marine or animal origin.

Activated Wax. This invention aims in particular to obtain a fatty alcohol-enriched wax (preferably jojoba oil wax, abbreviated "jojoba wax"), as defined above. The fatty alcohols present in the wax thus enriched act as the active cosmetic ingredients, advantageously in combination with the diacylglycerols of the activated fat/oil (see above), in the context of a cutaneous application. In other words, the fatty alcohol-enriched wax has a modified structure and an increased biological (cosmetic) activity at the cutaneous level. This is why wax thus enriched is also called activated wax.

Lipase of *Carica papaya*. Lipases (triacylglycerol hydrolase; EC.3.1.1.3) are reversible enzymes which, in the reaction's most favorable sense, hydrolyze the glycerol esters. These enzymes can also be classified into several groups, according to their different specificities: specificity with respect to the substrate; position specificity or stereospecificity; specificity with regard to the nature of fatty acids or typo-selectivity; positional specificity or stereospecificity. In this invention, stereospecific lipase of the sn3 type is used. This lipase thus hydrolyzes the triglycerides by preferentially forming 1-2 diacylglycerol. The lipase used may be of plant origin (example: *Carica papaya*) or microbial (example: *Penicelium cyclopium*). The technological platform developed by the Applicant is based on the use of *Carica papaya* lipase (Villeneuve et al., JAOCS, 72, 6:753.1995).

papaya (*Carica papaya*) is grown mainly in tropical and subtropical regions around the world. *papaya* is a member of the Caricaceae family, which belongs to the Brassicales family. The latex of *Carica papaya* is already known for its endopeptidases, a rich source of cysteine including papain, chymopapain and caricain. These proteinases can be extracted as water soluble latex proteins. The presence of lipase activity has been reported by Giordani et al. Until recently, all attempts to solubilize enzymatic activity from this latex fraction have failed. *Carica papaya* latex lipase (CPL) has therefore traditionally been considered a "naturally immobilized" biocatalyst. A dry powder containing lipase activity can be obtained after washing the latex particles with water and centrifuging. The stereospecificity and typo-selectivity of the *Carica papaya* latex raw sap were studied both during hydrolysis and during acyl transfer reactions. During the hydrolysis process, a 1,3-stereospecific activity was determined by this biocatalyst, with preferably a sn-3 stereo activity.

In the context of its experimental procedures, the Applicant has demonstrated a certain typo-selectivity of this lipase for fatty acids, this invention, under the experimental conditions described, orienting it to triacylglycerols having long chain fatty acids, of a length of between 18 and 20, and having between 0 and 3 unsaturations. Indeed, tests carried out previously have shown that under the operating conditions used in the invention, the yields for obtaining a 1,2-diacylglycerol-enriched oil are greater with an oil having predominantly fatty acids with a chain length of between 18 and 20 carbons and having unsaturations (olive oil for example) than with an oil whose saturated fatty acids have a chain length of between 8 and 10 carbons respectively (caprylic/capric triglycerides—Mygliol® 812), 12 and 16 carbons (animal butter), 16 and 18 carbons (palm oil). The results are summarized in Table 1 below.

TABLE 1

Comparison of DAG enrichment yields using the *Carica papaya* lipase from different fats

| Enriched Oil | Olive Oil | Myglyol 812 | Butter (Milk) | Palm Oil |
| --- | --- | --- | --- | --- |
| Acidity Index (mg/g) | 17.5 | 10.2 | 3.2 | 13.6 |
| 1,2 diacylglycerol Content | 15 | 6.8 | 1 | 8.9 |
| 1,3 diacylglycerol Content | 3 | 2 | 0 | 3.2 |

As indicated above, the technological platform developed by the Applicant is based on the use of *Carica papaya* lipase, and more particularly on the use of the water-insoluble fraction of its sap. However, this invention also extends, more broadly, to a diacylglycerol-enriched fat, by means of any suitable lipase (preferably by means of a stereospecific lipase of the sn3 type, for example of vegetable or microbial origin), advantageously with 1,2-diacylglycerols, preferably with 1,2-diacylglycerols of the formula (I) as defined above, said fat being selected from *Calophyllum inophyllum* oil (preferably virgin), raspberry oil (preferably virgin), *Camellia* oil (preferably virgin), evening primrose oil (preferably virgin), Brazil nut oil (preferably virgin) and baobab oil (preferably virgin), said fat being *Calophyllum inophyllum* oil (preferably virgin). Moreover, the invention also extends to a composition comprising, consisting essentially of, or consisting of, said diacylglycerol-enriched fat (advantageously 1,2-diacylglycerols, preferably 1,2-diacylglycerols of the formula (I) as defined above) and a fatty alcohol-enriched wax (preferably of the formula (III) as defined above).

*Carica papaya* Sap (also referred to as: "raw *Carica papaya* sap"). *papaya* sap is obtained from *Carica papaya* latex. The latex is collected by incising the still green fruits. The green fruit is superficially cut to collect the white latex that solidifies upon contact with the air. It is mainly composed of proteins including endopeptidase enzymes (raw papain=papain, chymopapains, *papaya* proteinase; papain being a protein of 212 amino acids for a molecular weight of 23000 daltons), a lipase (*Carica papaya* lipase, called *Carica papaya* lipase in English; see Villeneuve et al. *JAOCS*, 72, 6:753. 1995), as well as sugars and vitamins.

Appendages. Appendages are visible protective products of the epidermis, characterized by intense keratinization. Hair, teeth, nails and hair are appendages.

(see Table 2 above). In a second step, the proteins obtained by the separation method have been characterized more precisely. Thus, after studying protease and lipase enzymatic activities, it was possible to determine the molecular weight of the proteins present in these two fractions. The amount of protein present in the raw sap as well as in each of the fractions was determined according to the Kjeldahl method and is reported in Table 3 below. Protease activity and lipolytic activity were then measured for *papaya* sap as well as in water soluble and water-insoluble fractions.

TABLE 3

Specific and overall enzymatic activities of *papaya* sap as well as water soluble and water insoluble fractions

|  | Proteolytic Activity | | | Lipolytic Activity | | |
| --- | --- | --- | --- | --- | --- | --- |
|  | Raw *Papaya* Sap | Soluble Fraction | Insoluble Fraction | Raw *Papaya* Sap | Soluble Fraction | Insoluble Fraction |
| Enzymatic Activity (U/mg Dry Matter) | 1.5 | 1.35 | 0.1 | 0.67 | Undetectable | 0.66 |
| Specific Enzymatic Activity (U/mg Protein) | 2.35 | 2.4 | 1.3 | 1.05 | / | 7.45 |
| Purification Factor | / | 1.02 | / | / | / | 7.1 |
| Total Enzymatic Activity | 150 | 134 | 11 | 67 | / | 60 |

Skin. Within the meaning of this invention, the skin is understood in the broad sense as the body component constituting the coating of the body and includes notably the scalp (skin of the skull covered with hair).

Characterization of Purified *papaya* Sap, and More Particularly of the Water-Insoluble Fraction (Non-Water-Soluble) of this *papaya* Sap When dried *papaya* sap was suspended in water, the enzymes exhibiting the lipolytic and protease activities exhibited different solubilities: the proteases being soluble unlike the enzymes responsible for the lipase activity (Giordani et al., 1991). This property made it possible to partially separate *papaya* sap into two fractions (see Table 2 below).

TABLE 2

Study and characterization of the fractionation of *papaya* sap

|  | Dry matter | | Proteins | |
| --- | --- | --- | --- | --- |
|  | Proportion | Total Amount/Fraction | Percentage/ Dry matter | Total Amount/Fraction |
| Raw *Papaya* Sap | 82% | 82% | 78% | 64.5% |
| Insoluble Fraction | 19% | 17% | 47% | 8% |
| Soluble Fraction | 7% | 59% | 95% | 56% |

The fractionation of *papaya* sap has been characterized by the dry matter content as well as the protein content of the fractions obtained, these values are compared with those of the sap. The sap used has 18% moisture, its suspension is 10% in water and the separation of the two fractions by centrifugation results in the recovery of 92% of the starting dry matter and 99.7% of the proteins initially present. Among these proteins, 88% are found in the water-soluble fraction and 12% in the water-insoluble particulate fraction Suspension of *papaya* sap in water makes it possible to efficiently separate the protease activity from the lipase activity initially contained in the sap. Indeed, approximately 90% of the proteolytic activity and the lipolytic activity present initially are found respectively in the water soluble and water insoluble fractions.

The molecular weight of proteins present in *papaya* sap and whose water soluble and water insoluble fractions were determined on a 12% polyacrylamide gel under denaturing and reducing conditions. The electrophoretic profile thus obtained is shown in FIG. 1. Track M corresponds to a molecular weight marker (Invitrogen); track 1 corresponds to *papaya* sap; track 2 corresponds to the fraction in water of *papaya* sap; track 3 corresponds to the water-soluble fraction of this *papaya* sap and track 4 corresponds to the commercially purchased papain (Fluka).

Molecular weights of the main proteins observed were determined by correlation with those of the molecular weight marker using the representation log PM=f(Rf) (Rf=migration distance from protein/migration distance from the front of the gel).

These molecular weights are presented below, in Table 4.

TABLE 4

Molecular weights of proteins present in *papaya* sap, insoluble and water-soluble fractions, as well as in commercial papain.

|  | Raw Dried *Papaya* Sap | Insoluble Fraction | Soluble Fraction | Commercial Purified Papain |
| --- | --- | --- | --- | --- |
| Molecular Weight of Protein (kDa) | 35 | 23 | 35 | 35 |
|  | 23 |  | 28 | 23 |
|  | 22 |  | 23 | 22 |
|  | 18 |  | 22 | 18 |
|  |  |  | 18 | 15 |
|  |  |  | 15 |  |

*papaya* sap has four major proteins of molecular weight of 18, 22, 23 and 35 kDa respectively. The water insoluble fraction appears to be composed of a single protein having a molecular weight of 23 kDa. Since the water-soluble fraction of six proteins having a molecular weight of 15, 18, 22, 23, 28 and 35 kDa, the presence of a protein of 15 kDa must be due to a hydrolysis occurring during the suspension of the *papaya* sap. Commercial papain, which has no lipolytic activity, is made up of the same five protein forms as the *papaya* sap. The similarity between the electrophoretic profiles is certainly due to the fact that this commercial extract is a mixture of *papaya* sap endopeptidases in the form of proenzymes and/or mature enzymes.

Based on these results, the *Carica papaya* lipase appears to have a molecular weight of 23 kDa. However, a protein of the same molecular weight is also present in the water-soluble fraction and the commercial papain wherein a single protease activity has been revealed.

Characterization by Western Blot

An analysis of these same samples by Western Blot was then performed in order to identify the molecular weight of the proteins corresponding to papain-type activities.

The antibody used, a polyclonal antibody derived from goat serum that targets papain (Rockland, anti-Papain [*Carica papaya*]) mainly reveals a protein of 35 kDa. Weaker signals are observed for proteins of molecular weight between 15 and 28 kDa.

Papain is described to have a molecular weight ranging from 21 to 23 kDa (Azarkan et al., 2003). The antibody used apparently bonded to the propapain, the proenzyme precursor of papain possessing an N-terminal region (134 amino acids) followed by the mature enzyme composed of 212 amino acids. Indeed, this proenzyme consists of 345 amino acids (Taylor et al., 1999, Azarkan et al., 2003).

The more precise analysis of low intensity signals makes it possible to identify the presence of a less specific binding of the antibody to proteins having a molecular weight of 28 kDa for the insoluble and water-insoluble fractions as well as for a protein of 22 kDa for the water-soluble fraction.

For the water-insoluble fraction, the anti-papain antibody did not bind to the protein having a molecular weight of 23 kDa. This confirms that this protein is not a protease of the papain type but the lipase of *Carica papaya*.

Characterization by Zymogram Gel

The Zymogram gel technique makes it possible to determine the presence of enzymes in a protein mixture by highlighting their own activity. A specific substrate is previously included in the polyacrylamide gel, the enzymes forming separate tracks and revealed by the same reaction are called isozymes.

The implementation of two Zymogram gels (lipolytic and proteolytic) was considered in order to locate the presence of proteases and *Carica papaya* lipase in the various extracts.

Zymogram to Reveal Proteases

Figure 3:
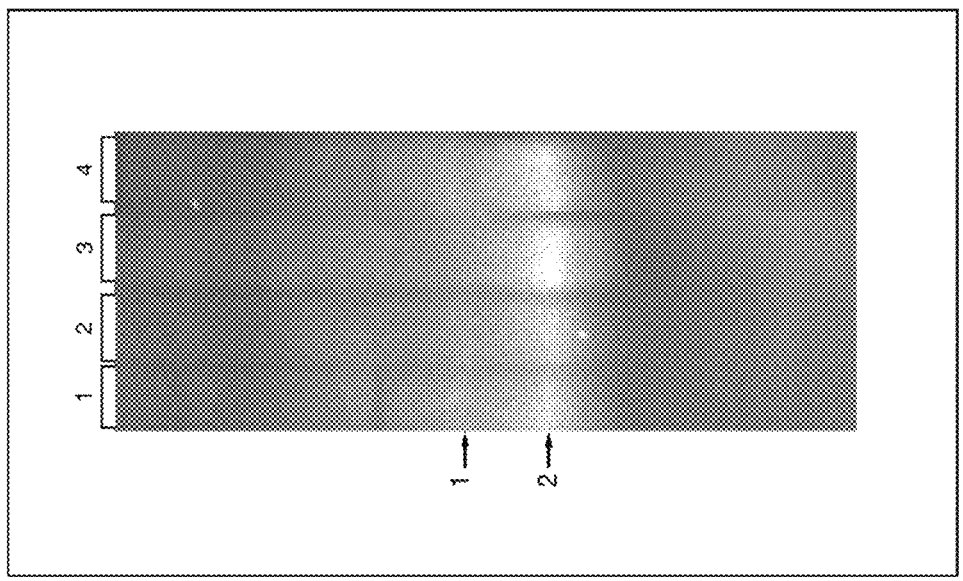
FIG. 3 is a 12% polyacrylamide Zymogram gel that contains 10% casein for protease detection; the Zymogram gel upon which the *papaya* sap (1), the water-insoluble fraction of *papaya* sap (2), the water-soluble fraction of *papaya* sap (3), standard papain (Sigma, Ref P4752) (5) is placed; this Zymogram gel being stained with Coomassie blue.

The Novex Casein Zymogram Zymogram gel used is composed of a separation gel composed of 12% polyacrylamide and containing 10% casein, a potential substrate for proteases. This gel is produced under non-reducing conditions in order to preserve enzymatic activities. Enzymes with proteolytic activity will locally hydrolyze the gel casein. After staining the gel with Coomassie blue, the zones where the proteins have been hydrolyzed are highlighted by their white color on a uniform blue background, as shown in FIG. 3. In this FIG. 3, the track 1 corresponds to the *papaya* sap, track 2 corresponds to the water-insoluble fraction of *papaya* sap, track 3 corresponds to the water-soluble fraction of the *papaya* sap and track 4 corresponds to the commercially purchased papain (Fluka).

The hydrolysis of casein, and therefore the presence of a more or less important protease activity, is observed for all the fractions analyzed (FIG. 3). Two isoforms are observed, isoform 2 having a greater intensity for the water-soluble fraction and the commercial papain.

Zymogram to Reveal Lipases

The production of Zymograms for detecting lipase enzyme activity is more complex than for proteases. The literature describes a system consisting of two gels, a first one wherein the proteins are separated and a second containing the substrate (Gilbert et al., 1991, Abousalham et al., 2000). In a first step, the proteins migrate on a polyacrylamide gel under native conditions. Then, the presence of lipases is revealed by applying an overlayer composed of a second polyacrylamide gel containing both the lipid substrate and a colored indicator, Victoria Blue, the color of which is blue in an acid medium and red in basic medium (Yadav et al., 1997). In this type of Zymogram, the presence of lipase activity is therefore displayed by the appearance of a blue color corresponding to the hydrolysis zones of the triacylglycerols of olive oil, and therefore to the production of oleic acid.

Two polyacrylamide gels are implemented in parallel. A first control gel is stained with Coomassie blue (FIG. 4A) and makes it possible to display the migration profile of the proteins in a non-denaturing condition. In parallel, a second Zymogram gel is revealed with the overlayer containing the substrate (see FIG. 4B).

Figure 4B:
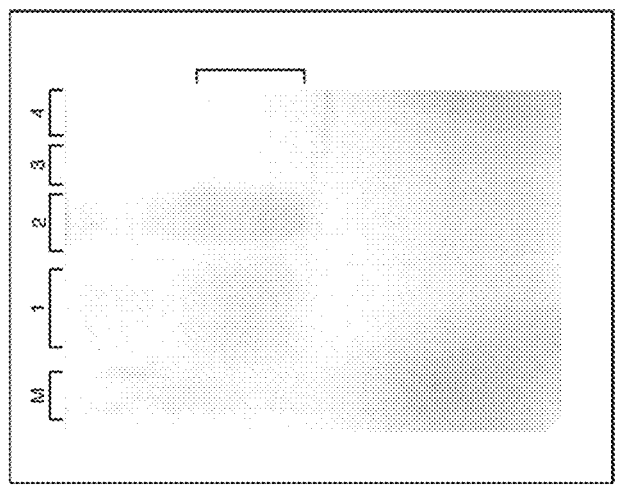
FIG. 4B is a Zymogram gel in non-denaturing condition on a 14% polyacrylamide gel revealed by covering a gel composed of olive oil and Victoria blue (B); gel Zymogram upon which were placed the *papaya* sap (1), the water-insoluble fraction of *papaya* sap (2), the water-soluble fraction of *papaya* sap (3), the commercial papain (Sigma, ref. P4752) (4), as well as a molecular weight marker (M).
Figure 4A:
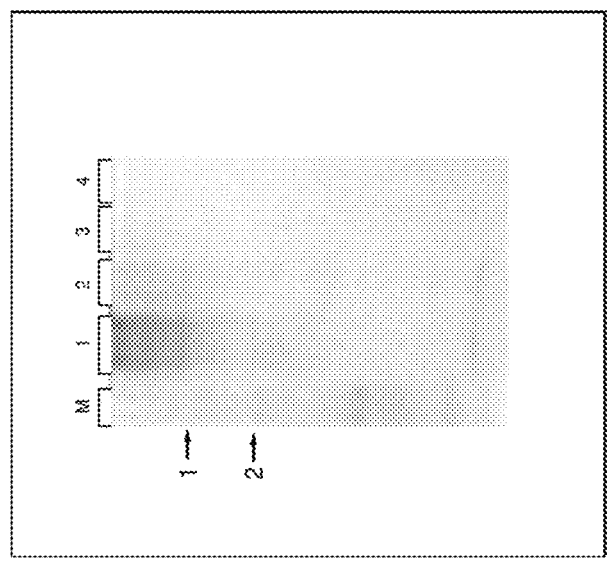
FIG. 4A is a Zymogram gel of a non-denaturing condition on a 14% polyacrylamide gel revealed with Coomassie blue; Zymogram gel upon which were placed the *papaya* sap (1), the water-insoluble fraction of *papaya* sap (2), the water-soluble fraction of *papaya* sap (3), commercial papain (Fluka) (4), as well as a molecular weight marker (M)

More specifically, FIG. 4A represents a Zymogram gel in non-denaturing condition on 14% polyacrylamide gel, revealed in Coomassie blue, and FIG. 4B represents a gel, in non-denaturing condition, on 14% polyacrylamide gel, revealed by covering a gel composed of olive oil and Victoria Blue (B).

The tracks for the Zymogram gels which are the objects of FIGS. 4A and 4B are identical and correspond to:

*papaya* sap for track 1,
the water-insoluble fraction of *papaya* sap for track 2,
the water-soluble fraction of *papaya* sap for track 3,
commercially purchased papain (Fluka) for track 4, and
to a molecular weight marker for the track (M).

Under non-denaturing conditions, the migration is not precise and only two protein entities are observed. (FIG. 4A).

With regard to the Zymogram itself, a blue coloration of the gel corresponding to an oleic acid production is observed for the *papaya* sap as well as for its water-insoluble fraction. Lipolytic activity is present only in these fractions.

Figure 2:
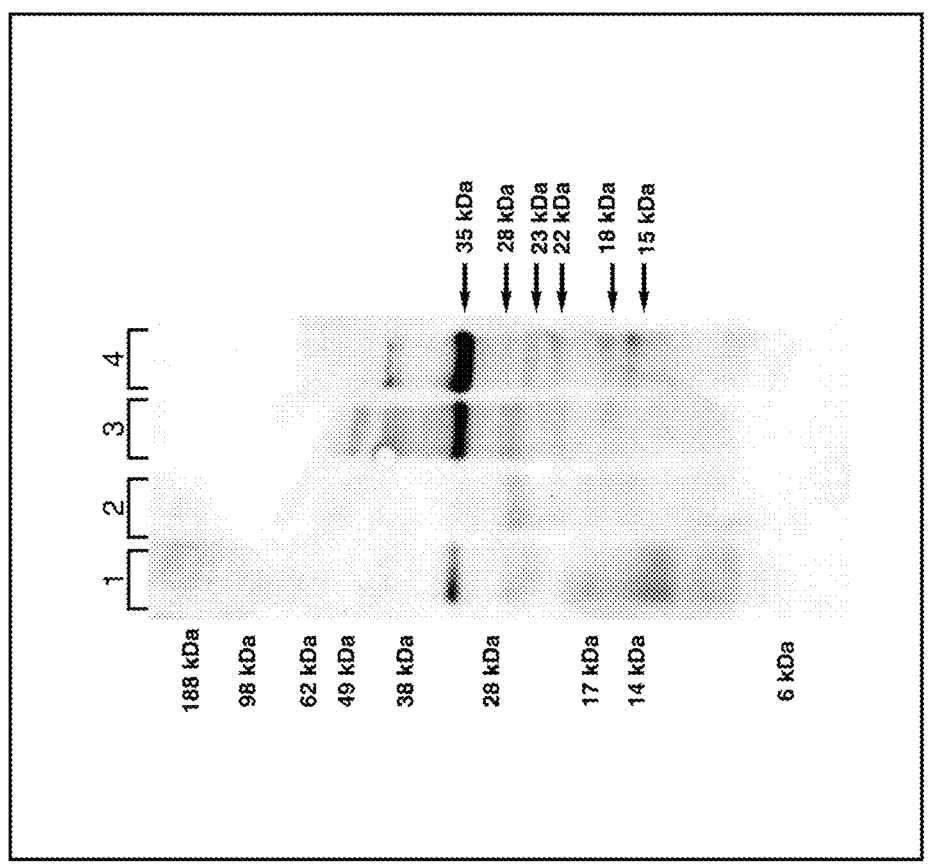
FIG. 2 is a photograph of the Western blot made on *papaya* sap (1), the water-insoluble fraction of *papaya* sap (2), the water-soluble fraction of *papaya* sap (3), and on commercial papain (4) with an antibody targeting papain.

Commercial papain has no lipase activity. The 23 kDa protein present in this extract therefore does not correspond to a lipase as the study of the enzymatic activities of the various fractions had already suggested (see FIG. 2 above).

This Zymogram study makes it possible to reveal proteolytic and lipolytic activity has confirmed that the *papaya* endopeptidases are a group of proteins with significant proteolytic enzymatic activity in the extracts studied.

This study also demonstrated that only *papaya* sap and its water-insoluble fraction have lipolytic activity that is bound to a protein of a molecular weight close to 23 kDa.

GPC (Gas Chromatography) Method Used to Quantify 1,2-Diacylglycerol

The assay is performed by gas chromatography using an internal standard, 1,3-dipalmitine. The analysis is carried out on an apolar type capillary column (HP5 (30 m×0.25 mm×0.25 mm), using Agilent 7890 gas chromatography controlled by ChemStation® software and having a flame ionization detector and an automatic injector.

The vector gas being helium (1.0 ml/min), the injector and the detector being heated to 330° C., the oven being programmed in isotherm at 325° C. for 30 minutes. The volume of sample injected being 1 μl. Under these conditions, 1,3-dipalmitine has a retention time of 13 minutes, respectively. The various diacylglycerols possess a retention time determined by the use of standards, previous bibliographic studies as well as preliminary analyzes carried out by gas chromatography coupled with mass spectrometry.

Determination of response coefficients, the working hypothesis being that all 1,2-diacylglycerols have the same response coefficient as 1,2-diolein, 1,2-diolein is used as the reference molecule.

Standard solutions: prepare four solutions as follows by weighing exactly the following masses:

TABLE 5

| Preparation of standard solutions | | | | |
|---|---|---|---|---|
| Product | Solution 1 | Solution 2 | Solution 3 | Solution 4 |
| 1,3-dipalmitine | 20 mg | 20 mg | 10 mg | 10 mg |
| 2-diolein | 20 mg | 10 mg | 20 mg | 10 mg |
| Pyridine | | 500 μL | | |
| HMDS | | 400 μL | | |
| TFA | | 50 μL | | |

Under our analysis conditions, the response coefficient of 1,2-diolein is 1.2315 (with a CV of 1.63%).

The enriched oil is then analyzed as follows:

TABLE 6

| Enriched Oil Analysis | | |
|---|---|---|
| Product | Solution 5 | Solution 6 |
| 1,2-Diacylglycerol-Enriched Oil | 100 mg | 100 mg |
| 1,3-dipalmitine | 15 mg | 15 mg |
| Pyridine | | 500 μL |
| HMDS | | 400 μL |
| TFA | | 50 μL |

The amount of 1,2-diacylglycerol contained in the solution is then determined as follows: Calculation of the mass of 1,2-diolein contained in the solution:

$$m(Ech)=[\alpha(Ech) \times A(Ech) \times m(SI)]/A(SI)$$

With: m=mass (in mg)
A=area under the peak
α=Response coefficient
Ech=sample (1,2-diacylglycerols)
SI=internal standard (1,3-dipalmitine)
Or:

$$m(1,2\text{-diacylglycerols})=[1,2315 \times \Sigma A(1,2\text{-diacylglycerols}) \times m(1,3\text{-dipalmitine})]/A(1,3\text{-dipalmitine})$$

Calculation of content: Content (%)=[$m$(1,2-diacylglycerols)/$m$(enriched oil)]×100

Example 1—Method for Obtaining the Water-Insoluble Fraction of Carica papaya Sap, Enriched with the Lipase of Carica papaya The lipase-enriched Carica papaya extract is obtained by producing a suspension of 100 g of dried raw papaya sap in 900 g of distilled water. The dried raw papaya sap is thus a biphasic suspension comprising suspended particles and a water-soluble fraction.

The mixture is agitated with an anchor-type agitator at a speed of 500 rotations per minute (rpm) for 2 hours at room temperature.

The water-insoluble (non-water-soluble) fraction of papaya sap (as characterized above) is separated from the soluble fraction by centrifugation of the mixture using a centrifuge, such as a plate centrifuge with a flow rate of 200 liters per hour, for 30 minutes.

The centrifugation pellet has the fraction of interest, i.e., the water-insoluble fraction of the raw papaya sap.

20 g of particulate fraction is thus obtained having a dry weight of 25%.

Example 2—Method for Preparing an Activated 1,2-Diacylglycerol-Enriched Oil

The mixture is prepared in two separate steps, then bringing together the products from these two methods in appropriate proportions, by simple mixing.

The 1,2-diacylglycerol-enriched oil is prepared from virgin Calophyllum inophyllum or Raspberry or Baobab or Evening Primrose or Brazil Nut or Camellia oil (because they offer excellent cutaneous cosmetic properties when they are activated, within the meaning of this invention) and an amount of water or saline solution containing a bivalent ion (such as a calcium or magnesium ion), representing from 0.5 to 50%, and preferably from 1 to 40%, of the volume of the oil. In a thermostatically controlled tank, this mixture is maintained at a temperature of between 30 and 70° C., preferably at a temperature of 50° C. This mixture is maintained under agitation using stator rotor type equipment in order to allow the formation of an emulsion between the oil and the water.

This mixture then remains under agitation in the presence of a given volume of the water-insoluble fraction of the Carica papaya lipase-enriched Carica papaya sap, obtained by implementing the method of Example 1, in a volume ratio water-insoluble fraction of Carica papaya sap/fat used comprised of between about 0.01 and about 0.2, advantageously between about 0.05 and 0.015, preferably about 0.1.

The agitation and the temperature are maintained for a period of between one and six hours (preferably four hours), that is to say for a time sufficient to maximize the amount of diacylglycerols formed.

Monitoring of the reaction is carried out by determining the conventional fat industry indicators (measurement of the acidity index NF EN ISO 660 and peroxide index NF ISO 3976), and by the use of chromatographic methods, notably by gas chromatography for qualifying and quantifying the diacylglycerol content.

The reaction medium is then purified by physicochemical purification techniques, the goal being to obtain a glossy, odorless 1,2-diacylglycerol-enriched oil that has a color closest to the oil initially used for the reaction.

The reaction medium is first filtered through a series of cellulose filters of decreasing porosity (500 to 250 μm). This initially allows the emulsion to breakdown and second to clarify the medium.

The residual water is then removed using an anhydrous magnesium sulfate desiccant. The oil thus obtained is then deodorized and rendered glossy with the help of an activated carbon (preferably CN1 type Cabot Norit® activated carbon).

The characteristics of the oil thus obtained has a common part inherent in the method described in the invention but also specific characteristics intrinsic to the nature of the oil used. The reaction medium mainly consists of unprocessed triglycerides, monoglycerides and 1,2- and 1,3-type diacylglycerols.

The oils are commonly characterized by an acidity index of between 15 and 50, a peroxide index of between 5 and 30 and a 1,2-diacylglycerol rate of between 5 and 30%.

The nature of the diacylglycerols obtained is based on the triacylglycerols initially present in the oil.

Tables 7 and 8 below make it possible to compare the acidity index, the peroxide index and the content of the 1,2-diacylglycerols and the 1,3-diacylglycerols of:
six virgin oils, particularly preferred in the sense of this invention, with
the same six virgin 1,2-diacylglycerol-enriched oils.

TABLE 7

Acidity Index, Peroxide Index, and 1,2-Diacylglycerol and 1,3-Diacylglycerol Content of the Six Preferred Virgin Oils

| | Initial Virgin Oil | | | | | |
|---|---|---|---|---|---|---|
| | Raspberry Oil | Baobab Oil | Evening Primrose Oil | Brazil Nut Oil | Camellia Oil | *Calophyllum Inophyllum* Oil |
| Acidity Index (mg/g) | 4 | 5 | 4 | 3 | 5 | 20 |
| Peroxide Index (meq $O_2$/Kg) | 15 | 14 | 10 | 14 | 12 | 8 |
| 1,2 diacylglycerol Content | 0.5 | 0 | 0 | 0 | 0.3 | 2 |
| 1,3 diacylglycerol Content | 0.5 | 0 | 0 | 0 | 0.4 | 1 |

TABLE 8

Acidity Index, Peroxide Index, and 1,2-Diacylglycerol and 1,3-Diacylglycerol Content of the Six Preferred Virgin Oils, after Enrichment with 1,2 DAG

| | Oil After Enrichment | | | | | |
|---|---|---|---|---|---|---|
| | 1,2 DAG Enriched-Raspberry Oil | 1,2 DAG Enriched-Baobab Oil | 1,2 DAG Enriched-Evening Primrose Oil | 1,2 DAG Enriched-Brazil Nut Oil | 1,2 DAG Enriched-*Camellia* Oil | 1,2 DAG Enriched-*Calophyllum Inophyllum* Oil |
| Acidity Index (mg/g) | 21.8 | 27.1 | 21.6 | 18.2 | 22.3 | 48.6 |
| Peroxide Index (meq $O_2$/Kg) | 29.6 | 2.5 | 25.8 | 18.7 | 12.9 | 4.2 |
| 1,2 diacylglycerol Content | 12 | 16 | 16.9 | 17.7 | 18 | 8 |
| 1,3 diacylglycerol Content | 2 | 3.5 | 2.5 | 2 | 2 | 1.5 |

Furthermore, a liquid fatty alcohol-enriched wax is prepared by implementing mutatis mutandis the preparation method described above, namely by using a wax instead of an oil and obtaining a fatty alcohol-enriched wax. For the sake of completeness, this method is described below:

Firstly jojoba wax is emulsified using a stator rotor type agitator, by mixing said wax with a quantity of water or saline solution containing a divalent ion such as a calcium or magnesium ion, representing from 0.5 to 50%, and preferably from 1 to 40% of the volume of wax, without pH modification. In a thermostatically controlled tank, this mixture is maintained at a temperature of between 30 and 70° C., preferably at a temperature of 50° C. This mixture is maintained under agitation using a stator rotor type equipment to allow the formation of a stable emulsion between the wax and the water.

This mixture then remains under agitation in the presence of a given volume of the water-insoluble fraction of the *Carica papaya* lipase-enriched *Carica papaya* sap, obtained by implementing the method of Example 1, in a volume ratio water-insoluble fraction of *Carica papaya* sap/fat used comprised of between about 0.01 and about 0.2, advantageously between about 0.05 and 0.015, preferably about 0.1.

The agitation and the temperature are maintained for a period of between one and six hours (preferably six hours), that is to say for a time sufficient to maximize the amount of fatty alcohols formed.

The reaction medium is first filtered through a series of cellulose filters of decreasing porosity (500 to 250 µm). This initially allows the emulsion to breakdown and second allows the medium to clarify.

The residual water is then removed using an anhydrous magnesium sulfate desiccant. The wax thus obtained is then deodorized and rendered glossy with the help of an activated carbon (preferably CN1 type Cabot Norit® activated carbon).

The reaction product is carried out by measuring the acidity index NF EN ISO 660 and by using chromatographic methods, notably by gas chromatography which makes it possible to qualify and quantify the content of fatty acids and fatty alcohols.

The product obtained is preferably characterized by a fatty alcohol content of between 2 and 4%, and an acidity index of 5 mg/g of wax.

In a particular embodiment of the invention, the composition corresponds to a 1,2-diacylglycerol-enriched oil (activated oil) or a mixture of several 1,2-diacylglycerol-enriched oils (activated oils).

In a particular embodiment of the invention, the composition corresponds to a fatty alcohol-enriched liquid wax (activated wax) or a mixture of several fatty alcohol-enriched liquid waxes (activated waxes).

In a preferred embodiment, the composition according to the invention is then obtained by simply mixing the 1,2-diacylglycerol-enriched oil (activated oil) and the fatty alcohol-enriched liquid wax (activated wax) in weight proportions comprised of between 100 and 90% of enriched oil and 0 to 10% enriched liquid wax.

Example 3 Cosmetic Formulations Including Activated Oil

3.1—Eye Contour Gel

TABLE 9

Composition of an "Eye Contour" gel according to the invention

| INGREDIENTS | BUSINESS NAME/INCI NAME | % w/w |
|---|---|---|
| Phase A | | |
| Purified Water | Water/Aqua | Qs 100 |
| Activated tamanu oil/activated jojoba wax blend according to Example 2 | (Proposed) Hydrolyzed Calophyllum Inophyllum Seed Oil and Hydrolyzed Jojoba Esters | 1.50 |
| Flexithix™ polymer | PVP | 3.00 |
| Phase B | | |
| Si-Tec™ DM 350 silicones | Dimethicone | 3.00 |
| Si-Tec™ RE-100 silicones | Cyclopentasiloxane (and) Dimethicone/Vinyltrimethylsiloxysilicate Crosspolymer | 10.00 |
| Cyclopentasiloxane | Cyclopentasiloxane | 5.00 |
| Phase C | | |
| Liquid germall plus preservative | Propylene glycol (and) Diazolidinyl urea (and) Iodopropynyl butylcarbamate | 0.50 |
| BPD-500 | HDI/Trimethylol hexyllactone crosspolymer & Silica | 0.50 |
| Total | | 100.00 |

Properties:

Appearance: Smooth, semi-transparent gel pH: 5.50-6.0

Viscosity (DO) 15000-25000 (Brookfield RVT/Spindle B/5 RPM/1 minute/25° C.)

This formula underwent a 3-month accelerated stability test in the laboratory. The preservation of this formula has been validated by a double efficacy test over 28 days. However, the preservatives have not been optimized to their lowest level of efficiency.

3.2—Biphasic Facial Serum

TABLE 10

Composition of a biphasic facial serum according to the invention

| INGREDIENTS | BUSINESS NAME/INCI NAME | % w/w |
|---|---|---|
| Phase A | | |
| Purified Water | Water/Aqua | Qs 100 |
| Phase B | | |
| Blanose™ 7H3SF CMC | Carboxymethylcellulose | 0.30 |
| Zemea* | Propanediol | 1.00 |
| Phase C | | |
| Rokonsal™/Liquapar™ MEP preservative | Phenoxyethand (and) Methylparaben (and) Ethylparaben (and) Propylparaben | 0.70 |
| Neomatrix™ biofunctional | Water/Aqua (and) Glycerin (and) Pentapeptide (proposed name) | 1.00 |
| Sodium Chloride | Sodium Chloride | 1.00 |
| Unicert* Blue 05601-J (sol. 0.1%) | Water/Aqua (and) CI 42090 (FD&C Blue No. 1) | 0.20 |
| Unicert* Yellow 08005-J (sol 0.1%) | Water/Aqua (and) CI 19140 (FD&C Yellow No. 5) | 0.60 |
| Phase D | | |
| Ceraphyl™ ODS ester | Octyldodecyl Stearate | 7.00 |
| Unicert* Green K7016-J | CI 61565 (D&C Green No. 6) | 0.006 |
| Phase E | | |
| Optiphen™ preservative | Phenoxyethanol (and) Caprylyl Glycol | 0.50 |
| Ceraphyl™ 375 ester | Isostearyl Neopentanoate | 3.00 |
| Activated tamanu oil/activated jojoba wax blend according to Example 2 | (Proposed) Hydrolyzed Calophyllum Inophyllum Seed Oil and Hydrolyzed Jojoba Esters | 2.50 |
| Smart* 5 | Isododecane (and) Hydrogenated tetradecenyl/methylpentadecene | 8.00 |
| DC* FZ-3196 | Caprylyl Methicone | 5.00 |
| PF Absolute Perfection | Perfum/Fragrance (and) Linalool | 0.10 |
| Total | | 100.00 |

Properties:

Appearance: Green and dark blue biphasic liquid—shake before use pH: 5.0-6.0

Viscosity (DO) N.A.

This formula underwent a 3-month accelerated stability test in the laboratory. The preservation of this formula has been validated by a double efficacy test over 28 days. However, the preservatives have not been optimized to their lowest level of efficiency.

Example 4—Study of the Expression of Cytokeratin in Ex Vivo Human Skin, in the Presence of Different Activated Oils According to the Invention

4.1—Introduction to Cytokeratins

Cytokeratins are proteins of the intermediate filaments, which together with other proteins form the cytoskeleton of the cells. These have many functions including the maintenance of epithelial structure, protection from injury, and communication with other cytoplasmic components (Fuertes L. et al., 2013).

They are expressed in pairs, with different expression profiles depending on their location and are numerically ranked from 1 to 20 according to their molecular weight and isoelectric point. Cytokeratins are classified into two groups (Fuertes L. et al., 2013):

Type I cytokeratins, which are acids and generally correspond to cytokeratins having a low molecular weight, Type II cytokeratins, which are basic and generally have a high molecular weight.

During the process of epidermal differentiation, the keratinocytes of the basal layer lose their proliferative potential, migrate to the upper layers and the expression of keratins 5 and 14 is interrupted while that of keratins 1 and 10 increases (Paladini R D et al., 1999).

4.2—Purpose of the Study

The purpose of this study is to determine the influence of various activated oils/activated wax blends according to the invention, obtained by implementing the method of Example 2, on the expression of cytokeratins in ex vivo human skin.

4.3—Oils Tested

The different oils tested are:

Activated tamanu oil (*Calophyllum inophyllum*)/activated jojoba wax blend (abbreviated in the rest of Example 4 as "activated tamanu oil") obtained by the method of Example 2, versus native virgin tamanu oil, Activated baobab oil/activated jojoba wax blend (abbreviated in the rest of Example 4 as "activated baobab oil") obtained by the method of Example 2, versus native virgin baobab oil, Activated raspberry oil/activated jojoba wax blend (abbreviated in the rest of Example 4 as "activated raspberry oil") obtained by the method of Example 2, versus native virgin raspberry oil, Activated evening primrose oil/activated jojoba wax blend (abbreviated in the rest of Example 4 as "activated evening primrose oil") obtained by the method of Example 2, versus native virgin evening primrose oil.

4.3—Protocol

Human skin samples that are 6 mm in diameter are cultured in air/liquid interface. The activated oils are diluted to 0.5% in the corresponding non-activated oil. 20 µL of oil are applied topically to the skin samples (only one application), then these biopsies are incubated for 24 hours at 37° C. At the end of the culturing, the human skin samples are included in optimal cutting temperature (OCT) gel. The OCT solidifies upon contact with the cold (liquid nitrogen). These blocks containing the skin samples are stored at −20° C.

Then 6 µm thick sections are taken. These sections of skin samples are then oven-dried at 37° C., and then fixed with acetone (pre-cooled to −20° C.).

Immunolabeling is performed using a pancytokeratin-specific mouse monoclonal antibody (Abcam, Ref. ab27988), followed by a fluorochrome-coupled anti-mouse secondary antibody (Invitrogen, Ref A21202), followed by sections of skin samples are then examined under an Epifluorescence microscope (Zeiss Axiovert 200M). A quantification of the fluorescence, from the photographs obtained, was carried out with Volocity software.

4.4—Results

Microscopic observations show a significantly more intense fluorescence in the epidermis of biopsies treated with activated tamanu oil, activated baobab oil, activated raspberry oil and activated evening primrose oil compared to the corresponding non-activated oil. The data obtained are presented below, in Tables 11-14.

TABLE 11

| Cytokeratin Expression (%) Activated Tamanu Oil Vs. Virgin Tamanu Oil | | |
|---|---|---|
| | 0.5% Activated Tamanu Oil | Virgin Tamanu Oil |
| Cytokeratin expression (%) | 123.3 ± 4.6 | 100 ± 4.7 |

TABLE 12

| Cytokeratin Expression (%) Activated Baobab Oil Vs. Virgin Baobab Oil | | |
|---|---|---|
| | 0.5% Activated Baobab Oil | Virgin Baobab Oil |
| Cytokeratin expression (%) | 112.7 ± 2.6 | 100 ± 3.1 |

TABLE 13

| Cytokeratin Expression (%) Activated Raspberry Oil Vs. Virgin Raspberry Oil | | |
|---|---|---|
| | 0.5% Activated Raspberry Oil | Virgin Raspberry Oil |
| Cytokeratin expression (%) | 124.7 ± 2.8 | 100 ± 2.2 |

TABLE 14

| Cytokeratin Expression (%) Activated Evening Primrose Oil Vs. Virgin Evening Primrose Oil | | |
|---|---|---|
| | 0.5% Activated Evening Primrose Oil | Virgin Evening Primrose Oil |
| Cytokeratin expression (%) | 124.8 ± 4.6 | 100 ± 4.2 |

Statistical analysis was performed versus the corresponding non-activated oil (mean±sem, n=8, ***: highly significant with Student's t-test).

Figure 5:
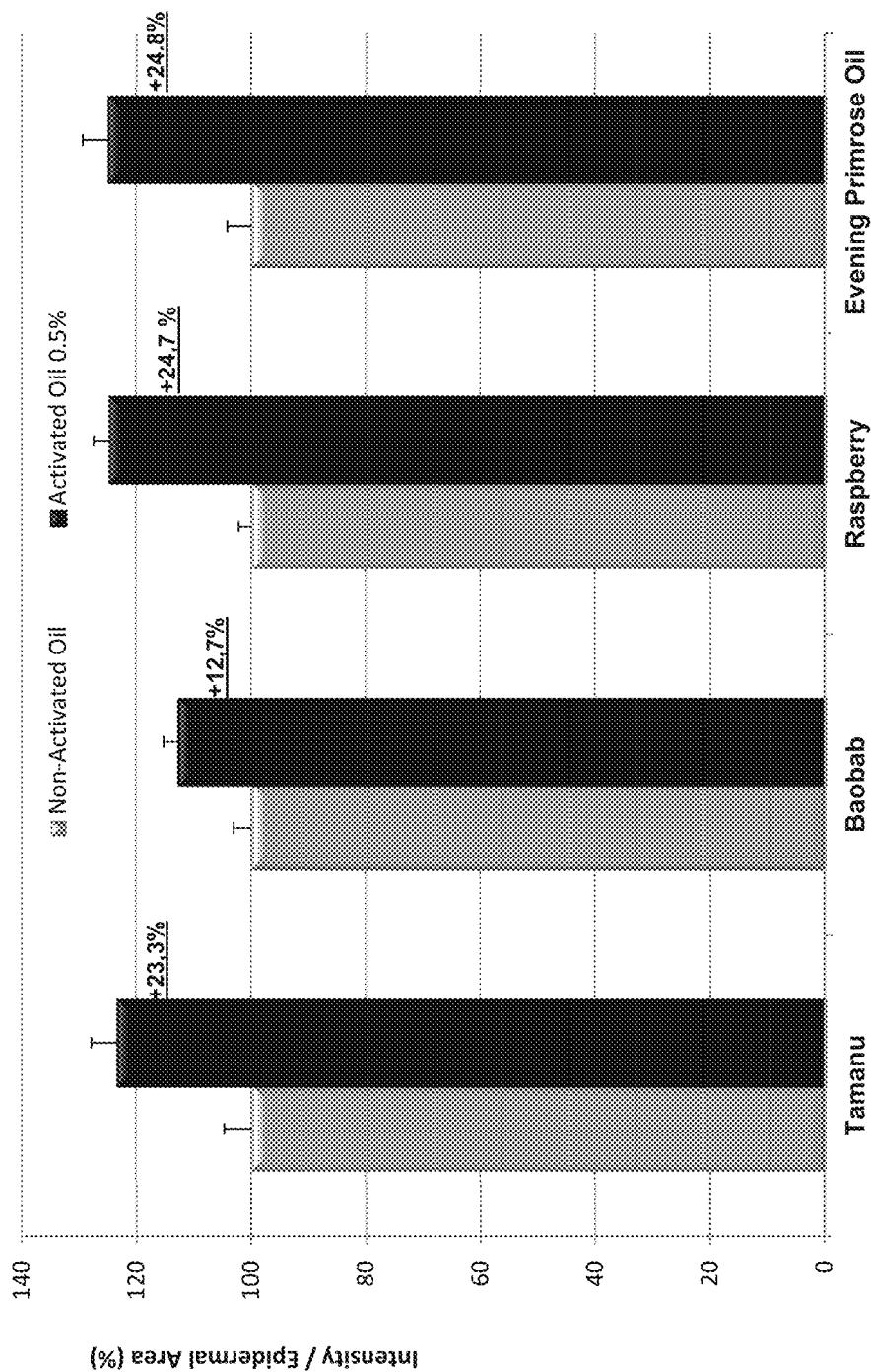
FIG. 5, for its part, is a graph showing quantification of pan cytokeratin labeling of 0.5% activated oils and inactivated oils of Tamanu, Baobab, Raspberry and Evening primrose in human skin samples.

In order to highlight the difference in expression observed between the activated oils and the corresponding virgin oils, the data obtained were plotted on the graph shown in FIG. 5.

4.5—Conclusions

The expression of cytokeratins is increased in ex vivo human skin by activated tamanu oil, activated baobab oil, activated raspberry oil and activated evening primrose oil.

Thus, these activated oils stimulate epidermal differentiation and therefore have interesting cosmetic properties.

4.6—Bibliographical References

Fuertes L., Santonja C., Kutzner H. and Requena L. Immunohistochemistry in Dermatopathology: a review of the most commonly used antibodies (Part I). *Actas Dermo-Sifiliográficas.* 104(2):99-127 (2013)

Paladini R. D. and Coulombe P. A. The functional diversity of epidermal keratins revealed by the partial rescue of the keratin 14 null phenotype by keratin 16. *The Journal of Cell Biology.* 146 (5):1185-1201 (1999)

The invention claimed is:

1. A method for obtaining a water-insoluble fraction of *Carica papaya* sap, enriched with *Carica papaya* lipase, the method comprising the following steps:

a) suspending dried *Carica papaya* sap in distilled water in a weight ratio of dried raw *Carica papaya*/distilled water of between 0.01 and 0.5, between 0.05 and 0.25, between 0.08 and 0.2, or 0.1, b) centrifuging the suspension obtained in step a) for a time period of between 5 minutes and 90 minutes, between 15 minutes and 60 minutes, or between 20 and 40 minutes, and at a rotation speed of between 2000 and 6000 rpm, between 3000 and 5000 rpm, or at 4000 rpm to obtain a pellet containing the water-insoluble fraction of the *Carica papaya* sap, enriched with *Carica papaya* lipase, c) recovering the pellet containing the water-insoluble fraction of the *Carica papaya* sap, enriched with *Carica papaya* lipase, and the method further comprising, after step a) and before step b), the following step:

a') stirring the suspension obtained in step a) for a time period of between 15 minutes and 240 minutes, a time period of between 30 minutes and 180 minutes, between 60 minutes and 150 minutes, or 120 minutes at room temperature.

2. The method according to claim 1, the method further comprising, after step b) and before step c), the following step:

b') drying the pellet until a particulate powder is obtained; wherein the water-insoluble fraction of *Carica papaya* sap, enriched with *Carica papaya* lipase, is recovered in step c), in the form of particulate powder.

* * * * *